US012629276B2

(12) United States Patent
Johannes et al.

(10) Patent No.: US 12,629,276 B2
(45) Date of Patent: May 19, 2026

(54) FLUID COLLECTION ASSEMBLIES INCLUDING A SKIRT

(71) Applicant: PUREWICK CORPORATION, El Cajon, CA (US)

(72) Inventors: Ashley Marie Johannes, Statham, GA (US); Pranav Challa, Atlanta, GA (US)

(73) Assignee: PUREWICK CORPORATION, Covington, GA (US)

( * ) Notice: Subject to any disclaimer, the term of this patent is extended or adjusted under 35 U.S.C. 154(b) by 543 days.

(21) Appl. No.: 17/759,697

(22) PCT Filed: Jan. 29, 2021

(86) PCT No.: PCT/US2021/015787

§ 371 (c)(1),
(2) Date: Jul. 28, 2022

(87) PCT Pub. No.: WO2021/155206

PCT Pub. Date: Aug. 5, 2021

(65) Prior Publication Data

US 2023/0049924 A1     Feb. 16, 2023

Related U.S. Application Data

(60) Provisional application No. 62/967,977, filed on Jan. 30, 2020.

(51) Int. Cl.
| | |
|---|---|
| *A61F 5/443* | (2006.01) |
| *A61F 5/44* | (2006.01) |
| *A61F 5/445* | (2006.01) |

(52) U.S. Cl.
CPC ............ *A61F 5/443* (2013.01); *A61F 5/4401* (2013.01); *A61F 5/4408* (2013.01); *A61F 5/445* (2013.01)

(58) Field of Classification Search
CPC ...... A61F 5/451; A61F 5/4401; A61F 5/4408; A61F 5/443
See application file for complete search history.

(56) References Cited

U.S. PATENT DOCUMENTS

| | | |
|---|---|---|
| 670,602 A | 3/1901 | Baker |
| 737,443 A | 8/1903 | Mooers |
| | (Continued) | |

FOREIGN PATENT DOCUMENTS

| | | |
|---|---|---|
| AU | 2018216821 A1 | 8/2019 |
| AU | 2021299304 A1 | 2/2023 |
| | (Continued) | |

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Ballard Spahr LLP

(57)     ABSTRACT

An example fluid collection assembly includes a fluid collection assembly defining an opening. The fluid collection assembly includes a fluid impermeable barrier defining at least a portion of a chamber and at least one porous material disposed in the chamber. The opening and the chamber of the fluid collection assembly are configured to receive at least a portion of a penis (e.g., at least the urethral opening of the penis). The fluid collection assembly also includes a skirt. The skirt is configured to attach the fluid collection assembly to an individual. To facilitate attachment to the individual, the skirt may exhibit a high flexibility. The high flexibility allows the skirt to be comfortably attached to the skin about the penis even when the size and/or topography of the skin about the penis varies and/or changes due to movement of the individual.

23 Claims, 7 Drawing Sheets

(56)                    References Cited

U.S. PATENT DOCUMENTS

| | | | |
|---|---|---|---|
| 1,015,905 A | 1/1912 | Northrop | |
| 1,032,841 A | 7/1912 | Koenig | |
| 1,178,644 A | 4/1916 | Johnson | |
| 1,387,726 A | 8/1921 | Karge | |
| 1,742,080 A | 12/1929 | Jones | |
| 1,979,899 A | 11/1934 | Obrien et al. | |
| 2,241,010 A | 5/1941 | Chipley | |
| 2,262,772 A | 11/1941 | Peder | |
| 2,326,881 A | 8/1943 | Packer | |
| 2,379,346 A | 6/1945 | Farrell | |
| 2,485,555 A | 10/1949 | Bester | |
| 2,571,357 A | 10/1951 | Charles | |
| 2,613,670 A | 10/1952 | Edward | |
| 2,616,426 A | 11/1952 | Adele | |
| 2,644,234 A | 7/1953 | Earl | |
| 2,648,335 A | 8/1953 | Chambers | |
| 2,789,560 A | 4/1957 | Weimer | |
| 2,859,786 A | 11/1958 | Tupper | |
| 2,944,551 A | 7/1960 | Carl | |
| 2,968,046 A * | 1/1961 | Duke | A61G 9/006 |
| | | | 604/149 |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,114,916 A | 12/1963 | Hadley | |
| 3,169,528 A | 2/1965 | Knox et al. | |
| 3,171,506 A | 3/1965 | Therkel | |
| 3,175,719 A | 3/1965 | Herndon | |
| 3,194,238 A | 7/1965 | Breece | |
| 3,198,994 A | 8/1965 | Hildebrandt et al. | |
| 3,221,742 A | 12/1965 | Egon | |
| 3,312,221 A | 4/1967 | Overment | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,434,565 A | 3/1969 | Fischer | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,608,552 A | 9/1971 | Broerman | |
| 3,613,123 A | 10/1971 | Langstrom | |
| 3,648,700 A | 3/1972 | Warner | |
| 3,651,810 A | 3/1972 | Ormerod | |
| 3,661,155 A | 5/1972 | Lindan | |
| 3,683,918 A | 8/1972 | Pizzella | |
| 3,699,815 A | 10/1972 | Holbrook | |
| 3,721,243 A | 3/1973 | Greth et al. | |
| 3,726,277 A | 4/1973 | Hirschman | |
| 3,742,952 A | 7/1973 | Magers et al. | |
| 3,742,953 A | 7/1973 | Lee | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,865,109 A | 2/1975 | Elmore et al. | |
| 3,881,486 A | 5/1975 | Fenton | |
| 3,881,489 A | 5/1975 | Hartwell | |
| 3,915,189 A | 10/1975 | Holbrook et al. | |
| 3,931,650 A | 1/1976 | Miller | |
| 3,964,786 A | 6/1976 | Mashuda | |
| 3,998,228 A | 12/1976 | Poidomani | |
| 3,999,550 A | 12/1976 | Martin | |
| 4,006,793 A | 2/1977 | Robinson | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,031,897 A | 6/1977 | Graetz | |
| 4,064,962 A | 12/1977 | Hunt | |
| 4,069,817 A | 1/1978 | Fenole et al. | |
| 4,084,589 A | 4/1978 | Kulvi | |
| 4,096,897 A | 6/1978 | Cammarata | |
| 4,116,197 A | 9/1978 | Bermingham | |
| 4,140,739 A | 2/1979 | Cotten | |
| 4,180,178 A | 12/1979 | Turner | |
| 4,187,953 A | 2/1980 | Turner | |
| 4,194,508 A | 3/1980 | Anderson | |
| 4,197,849 A | 4/1980 | Bostick | |
| 4,200,102 A * | 4/1980 | Duhamel | A61F 5/451 |
| | | | 604/353 |
| 4,202,058 A | 5/1980 | Anderson | |
| 4,203,503 A | 5/1980 | Bertotti et al. | |
| 4,209,076 A | 6/1980 | Bertotti et al. | |
| 4,223,677 A | 9/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,253,542 A | 3/1981 | Ruspa et al. | |
| 4,257,418 A | 3/1981 | Hessner | |
| 4,270,539 A | 6/1981 | Frosch et al. | |
| 4,280,498 A | 7/1981 | Jensen | |
| 4,281,655 A | 8/1981 | Terauchi | |
| 4,292,916 A | 10/1981 | Bradley et al. | |
| 4,330,239 A | 5/1982 | Gannaway | |
| 4,345,341 A | 8/1982 | Saito | |
| 4,349,029 A | 9/1982 | Mott | |
| 4,352,356 A | 10/1982 | Tong | |
| 4,360,933 A | 11/1982 | Kimura et al. | |
| 4,365,363 A | 12/1982 | Windauer | |
| 4,375,841 A | 3/1983 | Vielbig | |
| 4,387,726 A | 6/1983 | Denard | |
| 4,403,991 A | 9/1983 | Hill | |
| 4,421,511 A | 12/1983 | Steer et al. | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| 4,533,354 A | 8/1985 | Jensen et al. | |
| 4,533,357 A | 8/1985 | Hall | |
| D280,438 S | 9/1985 | Wendt | |
| 4,551,141 A | 11/1985 | Mcneil | |
| 4,553,968 A | 11/1985 | Komis | |
| 4,568,341 A | 2/1986 | Mitchell et al. | |
| 4,581,026 A | 4/1986 | Schneider | |
| 4,583,983 A | 4/1986 | Einhorn et al. | |
| 4,589,516 A | 5/1986 | Inoue et al. | |
| 4,601,716 A | 7/1986 | Smith | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A | 12/1986 | Martin | |
| 4,650,477 A | 3/1987 | Johnson | |
| 4,655,754 A | 4/1987 | Richmond et al. | |
| 4,656,675 A | 4/1987 | Fajnsztajn | |
| 4,681,570 A | 7/1987 | Dalton | |
| 4,681,572 A | 7/1987 | Tokarz et al. | |
| 4,681,577 A | 7/1987 | Stern et al. | |
| 4,692,160 A | 9/1987 | Nussbaumer | |
| 4,707,864 A | 11/1987 | Ikematsu et al. | |
| 4,713,065 A | 12/1987 | Koot | |
| 4,713,066 A | 12/1987 | Komis | |
| 4,723,953 A | 2/1988 | Pratt et al. | |
| 4,735,841 A | 4/1988 | Sourdet | |
| 4,743,236 A | 5/1988 | Manschot | |
| 4,747,166 A * | 5/1988 | Kuntz | A61F 5/455 |
| | | | 4/144.1 |
| 4,752,944 A | 6/1988 | Conrads et al. | |
| 4,759,753 A | 7/1988 | Schneider et al. | |
| 4,769,215 A | 9/1988 | Ehrenkranz | |
| 4,771,484 A | 9/1988 | Mozell | |

(56)                    References Cited

U.S. PATENT DOCUMENTS

| | | | |
|---|---|---|---|
| 4,772,280 A | 9/1988 | Rooyakkers | |
| 4,775,458 A | 10/1988 | Forester | |
| 4,784,654 A | 11/1988 | Beecher | |
| 4,790,830 A | 12/1988 | Hamacher | |
| 4,790,835 A | 12/1988 | Elias | |
| 4,791,686 A | 12/1988 | Taniguchi et al. | |
| 4,795,449 A * | 1/1989 | Schneider | A61F 5/441 |
| | | | 604/326 |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,813,943 A | 3/1989 | Smith | |
| 4,820,291 A * | 4/1989 | Terauchi | A61F 5/451 |
| | | | 4/144.3 |
| 4,820,297 A | 4/1989 | Kaufman et al. | |
| 4,841,728 A | 6/1989 | Jean et al. | |
| 4,846,818 A | 7/1989 | Keldahl et al. | |
| 4,846,819 A | 7/1989 | Welch | |
| 4,846,824 A | 7/1989 | Lassen et al. | |
| 4,846,909 A | 7/1989 | Klug et al. | |
| 4,865,595 A | 9/1989 | Heyden | |
| 4,880,417 A | 11/1989 | Yabrov et al. | |
| 4,882,794 A | 11/1989 | Stewart | |
| 4,883,465 A | 11/1989 | Brennan | |
| 4,886,498 A | 12/1989 | Newton | |
| 4,886,508 A * | 12/1989 | Washington | A61F 5/455 |
| | | | 604/347 |
| 4,886,509 A | 12/1989 | Mattsson | |
| 4,889,532 A | 12/1989 | Metz et al. | |
| 4,889,533 A | 12/1989 | Beecher | |
| 4,890,691 A | 1/1990 | Ching-ho | |
| 4,895,140 A | 1/1990 | Bellak | |
| 4,903,254 A | 2/1990 | Haas | |
| 4,904,248 A | 2/1990 | Vaillancourt | |
| 4,905,692 A | 3/1990 | More | |
| 4,911,262 A | 3/1990 | Tani et al. | |
| 4,930,997 A | 6/1990 | Bennett | |
| 4,936,838 A | 6/1990 | Cross et al. | |
| 4,950,262 A | 8/1990 | Takagi | |
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A | 3/1991 | Conkling et al. | |
| 5,004,463 A | 4/1991 | Nigay | |
| 5,013,308 A * | 5/1991 | Sullivan | A61F 5/453 |
| | | | 604/351 |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,102,404 A | 4/1992 | Goldberg et al. | |
| 5,112,324 A | 5/1992 | Wallace | |
| 5,134,994 A | 8/1992 | Say | |
| 5,137,033 A | 8/1992 | Norton | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,199,444 A | 4/1993 | Wheeler | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,979 A | 3/1994 | Delaurentis et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,457 A | 7/1994 | Cohen | |
| 5,330,459 A | 7/1994 | Lavon et al. | |
| 5,334,174 A | 8/1994 | Street | |
| 5,334,176 A | 8/1994 | Buenger et al. | |
| 5,340,840 A | 8/1994 | Park et al. | |
| 5,382,244 A | 1/1995 | Telang | |
| 5,397,315 A | 3/1995 | Schmidt et al. | |
| 5,409,014 A | 4/1995 | Napoli et al. | |
| 5,409,475 A * | 4/1995 | Steer | A61F 5/453 |
| | | | 604/352 |
| 5,411,495 A | 5/1995 | Willingham | |
| 5,423,784 A | 6/1995 | Metz | |
| 5,423,788 A | 6/1995 | Rollins et al. | |
| 5,437,836 A | 8/1995 | Yamada | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,593,389 A | 1/1997 | Chang | |
| 5,605,161 A | 2/1997 | Cross | |
| 5,614,699 A | 3/1997 | Yashiro et al. | |
| 5,618,277 A | 4/1997 | Goulter | |
| 5,628,735 A | 5/1997 | Skow | |
| 5,632,736 A | 5/1997 | Block | |
| 5,636,643 A | 6/1997 | Argenta et al. | |
| 5,637,104 A | 6/1997 | Ball et al. | |
| 5,662,633 A | 9/1997 | Doak et al. | |
| 5,674,212 A | 10/1997 | Osborn et al. | |
| 5,678,564 A | 10/1997 | Lawrence et al. | |
| 5,678,654 A | 10/1997 | Uzawa | |
| 5,681,297 A | 10/1997 | Hashimoto et al. | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,735,835 A | 4/1998 | Holland | |
| 5,735,837 A | 4/1998 | Ishikawa | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,873,869 A | 2/1999 | Hammons et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A * | 4/1999 | Birbara | A61F 5/4556 |
| | | | 604/319 |
| 5,895,349 A | 4/1999 | Tihon | |
| D409,303 S | 5/1999 | Oepping | |
| 5,911,222 A | 6/1999 | Lawrence et al. | |
| 5,956,782 A | 9/1999 | Olguin | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |

(56)                    References Cited

U.S. PATENT DOCUMENTS

| | | | |
|---|---|---|---|
| 6,105,174 A | 8/2000 | Karlsten et al. | |
| 6,113,582 A | 9/2000 | Dwork | |
| 6,117,163 A | 9/2000 | Bierman | |
| 6,123,398 A * | 9/2000 | Arai | B60T 8/17552 |
| | | | 303/151 |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,296,627 B1 | 10/2001 | Edwards | |
| 6,311,339 B1 * | 11/2001 | Kraus | A61F 5/451 |
| | | | 4/144.1 |
| 6,316,688 B1 | 11/2001 | Hammons et al. | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,395,956 B1 | 5/2002 | Glasgow et al. | |
| 6,398,742 B1 | 6/2002 | Kim | |
| 6,406,463 B1 | 6/2002 | Brown | |
| 6,409,712 B1 | 6/2002 | Dutari et al. | |
| 6,415,888 B2 | 7/2002 | An et al. | |
| 6,416,500 B1 | 7/2002 | Wada et al. | |
| 6,423,045 B1 | 7/2002 | Wise et al. | |
| 6,428,521 B1 | 8/2002 | Droll | |
| 6,428,522 B1 | 8/2002 | Dipalma et al. | |
| 6,446,454 B1 | 9/2002 | Lee et al. | |
| 6,461,340 B1 | 10/2002 | Lenker et al. | |
| 6,467,570 B1 | 10/2002 | Herold | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,526,603 B1 | 3/2003 | Murphy | |
| 6,540,729 B1 | 4/2003 | Wada et al. | |
| 6,547,771 B2 | 4/2003 | Robertson et al. | |
| 6,551,293 B1 * | 4/2003 | Mitchell | A61F 5/453 |
| | | | 604/347 |
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,037 B1 * | 10/2003 | Bennett | A61F 5/453 |
| | | | 604/353 |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,699,174 B1 | 3/2004 | Bennett | |
| 6,700,034 B1 | 3/2004 | Lindsay et al. | |
| 6,702,793 B1 | 3/2004 | Sweetser et al. | |
| 6,706,027 B2 * | 3/2004 | Harvie | A61F 5/453 |
| | | | 604/326 |
| 6,732,384 B2 * | 5/2004 | Scott | A47K 11/12 |
| | | | 4/144.1 |
| 6,736,977 B1 | 5/2004 | Hall et al. | |
| 6,740,066 B2 * | 5/2004 | Wolff | A61F 5/451 |
| | | | 604/323 |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,848,719 B2 | 2/2005 | Rowley | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2 * | 7/2005 | Harvie | A61F 5/451 |
| | | | 604/326 |
| 6,979,324 B2 | 12/2005 | Bybordi et al. | |
| 7,018,366 B2 * | 3/2006 | Easter | A61F 5/451 |
| | | | 604/327 |
| 7,066,411 B2 | 6/2006 | Male et al. | |
| 7,087,043 B2 | 8/2006 | Dolan | |
| 7,122,023 B1 | 10/2006 | Hinoki | |
| 7,125,399 B2 | 10/2006 | Miskie | |
| 7,131,964 B2 * | 11/2006 | Harvie | A61F 5/455 |
| | | | 604/326 |
| 7,135,012 B2 * | 11/2006 | Harvie | A61F 5/453 |
| | | | 604/326 |
| 7,141,043 B2 * | 11/2006 | Harvie | A61F 5/451 |
| | | | 604/326 |
| D533,972 S | 12/2006 | La | |
| 7,160,273 B2 | 1/2007 | Greter et al. | |
| 7,166,092 B2 * | 1/2007 | Elson | A61F 5/453 |
| | | | 604/352 |
| 7,171,699 B2 | 2/2007 | Ernest et al. | |
| 7,171,871 B2 | 2/2007 | Kozak | |
| 7,179,951 B2 | 2/2007 | Krishnaswamy-Mirle et al. | |
| 7,181,781 B1 * | 2/2007 | Trabold | A61F 5/455 |
| | | | 4/144.1 |
| 7,186,245 B1 | 3/2007 | Cheng et al. | |
| 7,192,424 B2 | 3/2007 | Cooper | |
| 7,219,764 B1 | 5/2007 | Forbes | |
| 7,220,250 B2 * | 5/2007 | Suzuki | A61F 5/451 |
| | | | 604/328 |
| D562,975 S | 2/2008 | Otto | |
| 7,335,189 B2 * | 2/2008 | Harvie | A61F 5/451 |
| | | | 604/326 |
| 7,358,282 B2 | 4/2008 | Krueger et al. | |
| 7,390,320 B2 * | 6/2008 | Machida | A61F 5/455 |
| | | | 4/144.1 |
| 7,438,706 B2 | 10/2008 | Koizumi et al. | |
| 7,488,310 B2 | 2/2009 | Yang | |
| 7,491,194 B1 | 2/2009 | Oliwa | |
| D591,106 S | 4/2009 | Dominique et al. | |
| 7,513,381 B2 | 4/2009 | Heng et al. | |
| 7,520,872 B2 | 4/2009 | Biggie et al. | |
| D593,801 S | 6/2009 | Wilson et al. | |
| 7,540,364 B2 | 6/2009 | Sanderson | |
| 7,549,511 B2 | 6/2009 | Marocco | |
| 7,549,512 B2 | 6/2009 | Newberry | |
| 7,585,293 B2 | 9/2009 | Vermaak | |
| 7,588,560 B1 | 9/2009 | Dunlop | |
| 7,637,905 B2 | 12/2009 | Saadat et al. | |
| 7,658,730 B2 * | 2/2010 | Conley | A61F 5/453 |
| | | | 604/350 |
| 7,665,359 B2 | 2/2010 | Barber | |
| 7,682,347 B2 | 3/2010 | Parks et al. | |
| 7,687,004 B2 | 3/2010 | Allen | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,699,831 B2 * | 4/2010 | Bengtson | A61M 27/00 |
| | | | 604/313 |
| 7,722,584 B2 | 5/2010 | Tanaka et al. | |
| 7,727,206 B2 | 6/2010 | Gorres | |
| 7,740,620 B2 | 6/2010 | Gilbert et al. | |
| 7,749,205 B2 * | 7/2010 | Tazoe | A61F 5/451 |
| | | | 604/320 |
| 7,755,497 B2 * | 7/2010 | Wada | A61F 5/451 |
| | | | 340/604 |
| 7,766,887 B2 | 8/2010 | Burns et al. | |
| 7,803,144 B1 | 9/2010 | Vollrath | |
| D625,407 S | 10/2010 | Koizumi et al. | |
| 7,806,879 B2 | 10/2010 | Brooks et al. | |
| 7,811,272 B2 | 10/2010 | Lindsay et al. | |
| 7,815,067 B2 | 10/2010 | Matsumoto et al. | |

(56)                    References Cited

U.S. PATENT DOCUMENTS

| | | | |
|---|---|---|---|
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2 | 5/2011 | Okabe et al. | |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,993,318 B2 | 8/2011 | Olsson et al. | |
| 8,015,627 B2 | 9/2011 | Baker et al. | |
| 8,016,071 B1 | 9/2011 | Martinus et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2 * | 3/2012 | Thevenin | A61F 13/84 |
| | | | 604/347 |
| 8,167,860 B1 | 5/2012 | Siegel | |
| 8,181,651 B2 | 5/2012 | Pinel | |
| 8,181,819 B2 | 5/2012 | Burney et al. | |
| 8,211,063 B2 * | 7/2012 | Bierman | A61M 25/02 |
| | | | 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 |
| | | | 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,343,125 B2 | 1/2013 | Kawazoe et al. | |
| 8,353,074 B2 | 1/2013 | Krebs | |
| 8,353,886 B2 | 1/2013 | Bester et al. | |
| D676,241 S | 2/2013 | Merrill | |
| 8,388,587 B1 | 3/2013 | Gmuer et al. | |
| 8,388,588 B2 | 3/2013 | Wada et al. | |
| D679,807 S | 4/2013 | Burgess et al. | |
| 8,425,482 B2 | 4/2013 | Khoubnazar | |
| 8,434,586 B2 | 5/2013 | Pawelski et al. | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,500,719 B1 | 8/2013 | Simpson et al. | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2 * | 10/2013 | Wada | A61F 5/4401 |
| | | | 604/361 |
| 8,551,062 B2 | 10/2013 | Kay | |
| 8,551,075 B2 * | 10/2013 | Bengtson | A61M 1/84 |
| | | | 604/543 |
| 8,568,376 B2 * | 10/2013 | Delattre | A61F 13/471 |
| | | | 604/385.01 |
| D694,404 S | 11/2013 | Burgess et al. | |
| 8,585,683 B2 * | 11/2013 | Bengtson | A61M 1/985 |
| | | | 604/543 |
| 8,586,583 B2 | 11/2013 | Hamblin et al. | |
| 8,652,112 B2 | 2/2014 | Johannison et al. | |
| 8,669,412 B2 | 3/2014 | Fernkvist et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 * | 10/2014 | Conway | A61F 5/4401 |
| | | | 604/346 |
| 8,881,923 B2 | 11/2014 | Higginson | |
| 8,882,731 B2 * | 11/2014 | Suzuki | A61F 5/451 |
| | | | 604/327 |
| 8,936,585 B2 | 1/2015 | Carson et al. | |
| D729,581 S | 5/2015 | Boroski | |
| 9,028,460 B2 * | 5/2015 | Medeiros | A61F 5/451 |
| | | | 604/347 |
| 9,056,698 B2 | 6/2015 | Noer | |
| 9,078,792 B2 | 7/2015 | Ruiz | |
| 9,145,879 B2 | 9/2015 | Pirovano et al. | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,233,020 B2 | 1/2016 | Matsumiya | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,381,108 B2 | 7/2016 | Longoni et al. | |
| 9,382,047 B2 | 7/2016 | Schmidtner et al. | |
| 9,402,424 B2 | 8/2016 | Roy | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| 9,623,159 B2 | 4/2017 | Locke | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,709,048 B2 | 7/2017 | Kinjo | |
| 9,713,547 B2 | 7/2017 | Lee et al. | |
| 9,732,754 B2 | 8/2017 | Huang et al. | |
| 9,737,433 B2 | 8/2017 | Joh | |
| 9,752,564 B2 | 9/2017 | Arceno et al. | |
| 9,788,992 B2 | 10/2017 | Harvie | |
| D804,907 S | 12/2017 | Sandoval | |
| 9,868,564 B2 | 1/2018 | Mcgirr et al. | |
| D814,239 S | 4/2018 | Arora | |
| D817,484 S | 5/2018 | Lafond | |
| 9,968,908 B2 | 5/2018 | Ladrech et al. | |
| 10,010,393 B1 | 7/2018 | Nguyen et al. | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/443 |
| 10,258,517 B1 | 4/2019 | Maschino et al. | |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 * | 8/2019 | Newton | A61F 5/4404 |
| 10,376,407 B2 | 8/2019 | Newton | |
| 10,390,989 B2 * | 8/2019 | Sanchez | A61D 99/00 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,500,108 B1 | 12/2019 | Maschino et al. | |
| 10,502,198 B2 | 12/2019 | Stumpf et al. | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| RE47,930 E | 4/2020 | Cho | |

(56)                    References Cited

U.S. PATENT DOCUMENTS

| | | | |
|---|---|---|---|
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| 10,799,386 B1 * | 10/2020 | Harrison, Sr. | A61F 5/441 |
| 10,806,623 B2 | 10/2020 | VanMiddendorp et al. | |
| 10,806,642 B2 | 10/2020 | Tagomori et al. | |
| D901,214 S | 11/2020 | Hu | |
| 10,849,799 B2 | 12/2020 | Nishikawa et al. | |
| 10,857,025 B2 * | 12/2020 | Davis | A61F 5/451 |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 * | 3/2021 | Newton | A61F 5/4404 |
| 10,973,378 B2 | 4/2021 | Ryu et al. | |
| 10,973,678 B2 * | 4/2021 | Newton | A61M 1/88 |
| 10,974,874 B2 | 4/2021 | Ragias et al. | |
| 11,000,401 B2 | 5/2021 | Ecklund et al. | |
| 11,002,165 B2 | 5/2021 | Poulin | |
| D923,365 S | 6/2021 | Wang | |
| 11,026,829 B2 * | 6/2021 | Harvie | A61M 25/0017 |
| 11,027,900 B2 | 6/2021 | Liu | |
| 11,045,346 B2 | 6/2021 | Argent et al. | |
| D928,946 S * | 8/2021 | Sanchez | D24/122 |
| 11,090,183 B2 | 8/2021 | Sanchez et al. | |
| 11,160,695 B2 | 11/2021 | Febo et al. | |
| 11,160,697 B2 | 11/2021 | Maschino et al. | |
| 11,168,420 B2 | 11/2021 | Kinugasa et al. | |
| 11,179,506 B2 | 11/2021 | Barr et al. | |
| 11,199,116 B2 | 12/2021 | Ostromecki et al. | |
| 11,207,206 B2 | 12/2021 | Sharma et al. | |
| 11,226,376 B2 | 1/2022 | Yamauchi et al. | |
| 11,253,389 B2 | 2/2022 | Sharma et al. | |
| 11,253,407 B2 | 2/2022 | Miao et al. | |
| 11,326,586 B2 | 5/2022 | Milner et al. | |
| 11,369,508 B2 | 6/2022 | Ecklund et al. | |
| 11,369,524 B2 | 6/2022 | Hubbard et al. | |
| 11,376,152 B2 * | 7/2022 | Sanchez | A61D 99/00 |
| 11,382,786 B2 * | 7/2022 | Sanchez | A61F 5/4404 |
| 11,382,788 B2 | 7/2022 | Hjorth et al. | |
| 11,389,318 B2 | 7/2022 | Radl et al. | |
| 11,395,871 B2 | 7/2022 | Radl et al. | |
| 11,399,990 B2 | 8/2022 | Suyama | |
| 11,426,303 B2 * | 8/2022 | Davis | A61F 5/4408 |
| 11,504,265 B2 | 11/2022 | Godinez et al. | |
| 11,529,252 B2 * | 12/2022 | Glithero | A61F 5/455 |
| 11,547,788 B2 | 1/2023 | Radl et al. | |
| 11,806,266 B2 | 11/2023 | Sanchez et al. | |
| 11,839,567 B2 | 12/2023 | Davis et al. | |
| D1,010,109 S | 1/2024 | Ecklund et al. | |
| 11,857,716 B2 | 1/2024 | Lee et al. | |
| 11,865,030 B2 | 1/2024 | Davis et al. | |
| 11,890,221 B2 | 2/2024 | Ulreich et al. | |
| 11,911,160 B2 | 2/2024 | Woodard et al. | |
| 11,925,575 B2 | 3/2024 | Newton | |
| 11,938,053 B2 | 3/2024 | Austermann et al. | |
| 11,944,740 B2 | 4/2024 | Hughett et al. | |
| 11,994,122 B2 | 5/2024 | Bodain | |
| 11,998,475 B2 * | 6/2024 | Becker | A61F 5/453 |
| 12,023,457 B2 | 7/2024 | Mann et al. | |
| 12,042,422 B2 | 7/2024 | Davis et al. | |
| D1,038,385 S | 8/2024 | Ecklund et al. | |
| 12,064,372 B2 | 8/2024 | Godinez et al. | |
| 12,070,432 B2 | 8/2024 | Tourchak et al. | |
| 12,090,083 B2 | 9/2024 | Ecklund et al. | |
| 12,121,468 B2 | 10/2024 | Sanchez et al. | |
| 12,133,813 B2 | 11/2024 | Ulreich et al. | |
| 12,138,195 B2 | 11/2024 | Alder et al. | |
| 12,186,229 B2 | 1/2025 | Davis et al. | |
| 12,193,962 B2 | 1/2025 | Newton et al. | |
| 12,245,966 B2 | 3/2025 | Newton | |
| 12,274,638 B2 | 4/2025 | Spector | |
| 2001/0037097 A1 | 11/2001 | Cheng et al. | |
| 2001/0037098 A1 | 11/2001 | Snyder | |
| 2001/0054426 A1 | 12/2001 | Knudson et al. | |
| 2002/0019614 A1 * | 2/2002 | Woon | A61F 13/53747 |
| | | | 604/378 |
| 2002/0026161 A1 | 2/2002 | Grundke | |
| 2002/0026163 A1 * | 2/2002 | Grundke | A61F 5/453 |
| | | | 604/347 |
| 2002/0042945 A1 | 4/2002 | Sands | |
| 2002/0087131 A1 | 7/2002 | Wolff et al. | |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2002/0193762 A1 | 12/2002 | Suydam | |
| 2003/0004436 A1 | 1/2003 | Schmidt et al. | |
| 2003/0032931 A1 | 2/2003 | Grundke et al. | |
| 2003/0032944 A1 | 2/2003 | Cawood | |
| 2003/0073964 A1 | 4/2003 | Palumbo et al. | |
| 2003/0074724 A1 | 4/2003 | Sands | |
| 2003/0120178 A1 | 6/2003 | Heki | |
| 2003/0129178 A1 | 7/2003 | Wegman et al. | |
| 2003/0157859 A1 | 8/2003 | Ishikawa | |
| 2003/0181880 A1 | 9/2003 | Schwartz | |
| 2003/0195484 A1 | 10/2003 | Harvie | |
| 2003/0204173 A1 | 10/2003 | Burns et al. | |
| 2003/0233079 A1 | 12/2003 | Parks et al. | |
| 2004/0006321 A1 | 1/2004 | Cheng et al. | |
| 2004/0015141 A1 | 1/2004 | Cheng et al. | |
| 2004/0056122 A1 | 3/2004 | Male et al. | |
| 2004/0084465 A1 | 5/2004 | Luburic | |
| 2004/0127872 A1 | 7/2004 | Petryk et al. | |
| 2004/0128749 A1 | 7/2004 | Scott | |
| 2004/0143229 A1 * | 7/2004 | Easter | A61F 5/451 |
| | | | 604/322 |
| 2004/0147863 A1 | 7/2004 | Diaz et al. | |
| 2004/0147894 A1 | 7/2004 | Mizutani et al. | |
| 2004/0147895 A1 | 7/2004 | Mizutani et al. | |
| 2004/0158221 A1 | 8/2004 | Mizutani et al. | |
| 2004/0176731 A1 | 9/2004 | Cheng et al. | |
| 2004/0176746 A1 | 9/2004 | Forral | |
| 2004/0181201 A1 | 9/2004 | Mizutani et al. | |
| 2004/0191919 A1 | 9/2004 | Unger et al. | |
| 2004/0194792 A1 | 10/2004 | Zhuang et al. | |
| 2004/0200936 A1 | 10/2004 | Opperthauser | |
| 2004/0207530 A1 * | 10/2004 | Nielsen | A61F 13/42 |
| | | | 340/573.5 |
| 2004/0236292 A1 * | 11/2004 | Tazoe | A61F 5/451 |
| | | | 604/317 |
| 2004/0243075 A1 | 12/2004 | Harvie | |
| 2004/0254547 A1 * | 12/2004 | Okabe | A61F 5/455 |
| | | | 604/317 |
| 2005/0010182 A1 | 1/2005 | Parks et al. | |
| 2005/0010197 A1 | 1/2005 | Lau et al. | |
| 2005/0033248 A1 * | 2/2005 | Machida | A61F 5/455 |
| | | | 604/327 |
| 2005/0065471 A1 | 3/2005 | Kuntz | |
| 2005/0070861 A1 * | 3/2005 | Okabe | A61F 5/4404 |
| | | | 604/327 |
| 2005/0070862 A1 * | 3/2005 | Tazoe | A61F 5/455 |
| | | | 604/327 |
| 2005/0082300 A1 | 4/2005 | Modrell et al. | |
| 2005/0097662 A1 | 5/2005 | Leimkuhler et al. | |
| 2005/0101924 A1 | 5/2005 | Elson et al. | |
| 2005/0119630 A1 | 6/2005 | Harvie | |
| 2005/0131361 A1 | 6/2005 | Miskie | |
| 2005/0137557 A1 | 6/2005 | Swiecicki et al. | |
| 2005/0137560 A1 | 6/2005 | Mizutani et al. | |
| 2005/0137561 A1 | 6/2005 | Mizutani et al. | |
| 2005/0148984 A1 | 7/2005 | Lindsay et al. | |
| 2005/0154360 A1 | 7/2005 | Harvie | |
| 2005/0177070 A1 | 8/2005 | Levinson et al. | |
| 2005/0197639 A1 | 9/2005 | Mombrinie | |
| 2005/0197645 A1 | 9/2005 | Karpowicz et al. | |
| 2005/0215969 A1 | 9/2005 | Mizutani et al. | |
| 2005/0273069 A1 | 12/2005 | Mizutani et al. | |
| 2005/0273920 A1 | 12/2005 | Marinas | |

(56)  References Cited

U.S. PATENT DOCUMENTS

| | | |
|---|---|---|
| 2005/0277903 A1 | 12/2005 | Mizutani et al. |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1* | 1/2006 | Suzuki .................... A61F 5/451 |
| | | 604/329 |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1* | 5/2006 | Vermaak .............. A61B 10/007 |
| | | 604/355 |
| 2006/0113334 A1 | 6/2006 | Mikhail et al. |
| 2006/0155214 A1* | 7/2006 | Wightman .............. A61F 5/455 |
| | | 600/574 |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0025886 A1 | 2/2007 | Yong |
| 2007/0038194 A1* | 2/2007 | Wada ...................... A61F 5/451 |
| | | 604/347 |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1* | 9/2007 | Carromba .............. A47K 11/12 |
| | | 4/144.4 |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1* | 2/2008 | Okabe ................... A61F 5/4404 |
| | | 604/378 |
| 2008/0041869 A1 | 2/2008 | Backaert |
| 2008/0077099 A1 | 3/2008 | House |
| 2008/0091153 A1* | 4/2008 | Harvie ................... A61F 5/451 |
| | | 604/318 |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1* | 11/2008 | Van Den Heuvel .... A61F 5/455 |
| | | 604/327 |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1* | 7/2009 | Dodge, II ......... A61F 13/53708 |
| | | 524/436 |
| 2009/0226541 A1 | 9/2009 | Scholz et al. |
| 2009/0234312 A1 | 9/2009 | Otoole et al. |
| 2009/0251510 A1 | 10/2009 | Noro et al. |
| 2009/0259206 A1* | 10/2009 | Kai ...................... A61F 5/4404 |
| | | 604/352 |
| 2009/0264840 A1 | 10/2009 | Virginio |
| 2009/0270822 A1* | 10/2009 | Medeiros ................ A61F 5/451 |
| | | 604/347 |
| 2009/0281510 A1 | 11/2009 | Fisher |
| 2009/0283982 A1 | 11/2009 | Thomas |
| 2009/0306610 A1 | 12/2009 | Van Den Heuvel et al. |
| 2010/0004612 A1* | 1/2010 | Thevenin ................ A61F 13/84 |
| | | 4/443 |
| 2010/0030189 A1 | 2/2010 | Fleming |
| 2010/0031429 A1 | 2/2010 | Kim et al. |
| 2010/0032789 A1 | 2/2010 | Schoen et al. |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1* | 7/2010 | Graauw ................ A61F 5/4556 |
| | | 604/347 |
| 2010/0198172 A1 | 8/2010 | Wada et al. |
| 2010/0211032 A1* | 8/2010 | Tsai ...................... A61F 5/453 |
| | | 604/319 |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1* | 2/2011 | Wada .................... A61F 5/4401 |
| | | 604/318 |
| 2011/0040271 A1* | 2/2011 | Rogers ................. A61F 5/4556 |
| | | 604/346 |
| 2011/0054426 A1 | 3/2011 | Stewart et al. |
| 2011/0060299 A1 | 3/2011 | Wada et al. |
| 2011/0060300 A1* | 3/2011 | Weig ...................... A61F 5/451 |
| | | 604/319 |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1* | 7/2011 | Wada ...................... A61F 13/42 |
| | | 604/385.01 |
| 2011/0198904 A1 | 8/2011 | Thomas et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton ................ A61F 5/453 |
| | | 128/885 |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0209225 A1 | 8/2012 | Hu et al. |
| 2012/0210503 A1* | 8/2012 | Anzivino, Sr. ....... A61F 5/4556 |
| | | 4/144.3 |
| 2012/0233761 A1 | 9/2012 | Huang |

(56) References Cited

U.S. PATENT DOCUMENTS

| | | | |
|---|---|---|---|
| 2012/0245541 A1* | 9/2012 | Suzuki | A61F 13/42 |
| | | | 604/319 |
| 2012/0245542 A1* | 9/2012 | Suzuki | A61F 13/84 |
| | | | 374/45 |
| 2012/0245547 A1 | 9/2012 | Wilcox et al. | |
| 2012/0253303 A1* | 10/2012 | Suzuki | A61F 13/42 |
| | | | 374/45 |
| 2012/0271259 A1 | 10/2012 | Ulert | |
| 2012/0296305 A1 | 11/2012 | Barraza Khaled et al. | |
| 2012/0316522 A1* | 12/2012 | Carter | A61F 5/449 |
| | | | 604/353 |
| 2012/0330256 A1 | 12/2012 | Wilcox et al. | |
| 2013/0006206 A1* | 1/2013 | Wada | A61F 13/535 |
| | | | 604/385.01 |
| 2013/0019374 A1 | 1/2013 | Schwartz | |
| 2013/0045651 A1 | 2/2013 | Esteves et al. | |
| 2013/0053804 A1 | 2/2013 | Soerensen et al. | |
| 2013/0096523 A1 | 4/2013 | Chang et al. | |
| 2013/0110059 A1 | 5/2013 | Kossow et al. | |
| 2013/0138064 A1 | 5/2013 | Stroebech et al. | |
| 2013/0144240 A1 | 6/2013 | Ellis | |
| 2013/0150813 A1 | 6/2013 | Gordon et al. | |
| 2013/0158494 A1 | 6/2013 | Ong et al. | |
| 2013/0165880 A1 | 6/2013 | Amos et al. | |
| 2013/0218112 A1 | 8/2013 | Thompson | |
| 2013/0245496 A1 | 9/2013 | Wells et al. | |
| 2013/0245586 A1* | 9/2013 | Jha | A61F 5/443 |
| | | | 604/352 |
| 2013/0274711 A1 | 10/2013 | O'Day | |
| 2013/0292537 A1 | 11/2013 | Dirico | |
| 2013/0330501 A1 | 12/2013 | Aizenberg et al. | |
| 2014/0005647 A1 | 1/2014 | Shuffler et al. | |
| 2014/0031774 A1* | 1/2014 | Bengtson | A61M 1/90 |
| | | | 604/319 |
| 2014/0039432 A1 | 2/2014 | Dunbar et al. | |
| 2014/0039440 A1 | 2/2014 | Doescher | |
| 2014/0058347 A1 | 2/2014 | Marquette | |
| 2014/0107599 A1 | 4/2014 | Fink et al. | |
| 2014/0157499 A1 | 6/2014 | Suzuki et al. | |
| 2014/0171889 A1 | 6/2014 | Hopman et al. | |
| 2014/0182051 A1* | 7/2014 | Tanimoto | A61G 9/006 |
| | | | 4/144.3 |
| 2014/0196189 A1 | 7/2014 | Lee et al. | |
| 2014/0257231 A1 | 9/2014 | Wang et al. | |
| 2014/0276501 A1 | 9/2014 | Cisko | |
| 2014/0303582 A1 | 10/2014 | Wright et al. | |
| 2014/0316381 A1 | 10/2014 | Reglin | |
| 2014/0325746 A1 | 11/2014 | Block | |
| 2014/0348139 A1 | 11/2014 | Gomez Martinez | |
| 2014/0352050 A1 | 12/2014 | Yao et al. | |
| 2014/0371628 A1 | 12/2014 | Desai | |
| 2015/0045757 A1 | 2/2015 | Lee et al. | |
| 2015/0047114 A1 | 2/2015 | Ramirez | |
| 2015/0048089 A1 | 2/2015 | Robertson | |
| 2015/0135423 A1 | 5/2015 | Sharpe et al. | |
| 2015/0157300 A1 | 6/2015 | Ealovega et al. | |
| 2015/0209188 A1 | 7/2015 | Scheremet et al. | |
| 2015/0209194 A1 | 7/2015 | Heyman | |
| 2015/0267862 A1 | 9/2015 | Mishler | |
| 2015/0290421 A1 | 10/2015 | Glickman et al. | |
| 2015/0290425 A1 | 10/2015 | Macy et al. | |
| 2015/0320583 A1 | 11/2015 | Harvie | |
| 2015/0329255 A1 | 11/2015 | Rzepecki | |
| 2015/0342799 A1 | 12/2015 | Michiels et al. | |
| 2015/0359660 A1* | 12/2015 | Harvie | A61F 5/441 |
| | | | 604/351 |
| 2015/0359996 A1 | 12/2015 | Arora et al. | |
| 2015/0366699 A1 | 12/2015 | Nelson | |
| 2016/0008193 A1 | 1/2016 | Schulke | |
| 2016/0029998 A1 | 2/2016 | Brister et al. | |
| 2016/0030228 A1 | 2/2016 | Jones | |
| 2016/0038356 A1 | 2/2016 | Yao et al. | |
| 2016/0051395 A1 | 2/2016 | Ugarte | |
| 2016/0058322 A1 | 3/2016 | Brister et al. | |
| 2016/0060001 A1 | 3/2016 | Wada et al. | |
| 2016/0100976 A1 | 4/2016 | Conway et al. | |
| 2016/0106604 A1* | 4/2016 | Timm | A61F 13/84 |
| | | | 604/385.01 |
| 2016/0113809 A1 | 4/2016 | Kim | |
| 2016/0135792 A1 | 5/2016 | Cai | |
| 2016/0136338 A1 | 5/2016 | Lee et al. | |
| 2016/0183689 A1 | 6/2016 | Miner | |
| 2016/0256022 A1 | 9/2016 | Le | |
| 2016/0270982 A1 | 9/2016 | Raycheck et al. | |
| 2016/0278662 A1 | 9/2016 | Brister et al. | |
| 2016/0357400 A1 | 12/2016 | Penha et al. | |
| 2016/0366699 A1 | 12/2016 | Zhang et al. | |
| 2016/0367226 A1* | 12/2016 | Newton | A01K 23/005 |
| 2016/0367411 A1 | 12/2016 | Justiz et al. | |
| 2016/0367726 A1 | 12/2016 | Gratzer | |
| 2016/0374848 A1* | 12/2016 | Sanchez | A61F 5/455 |
| | | | 604/319 |
| 2017/0007438 A1* | 1/2017 | Harvie | A61F 5/453 |
| 2017/0014560 A1 | 1/2017 | Minskoff et al. | |
| 2017/0042724 A1 | 2/2017 | Ugarte | |
| 2017/0042748 A1 | 2/2017 | Griffin | |
| 2017/0100276 A1 | 4/2017 | Joh | |
| 2017/0107312 A1 | 4/2017 | Hinayama et al. | |
| 2017/0128638 A1 | 5/2017 | Giezendanner et al. | |
| 2017/0136209 A1 | 5/2017 | Burnett et al. | |
| 2017/0143534 A1 | 5/2017 | Sanchez | |
| 2017/0165100 A1 | 6/2017 | Jackson et al. | |
| 2017/0165405 A1 | 6/2017 | Muser et al. | |
| 2017/0189225 A1 | 7/2017 | Voorhees et al. | |
| 2017/0202692 A1 | 7/2017 | Laniado | |
| 2017/0216081 A1 | 8/2017 | Accosta | |
| 2017/0238911 A1 | 8/2017 | Duval | |
| 2017/0246026 A1 | 8/2017 | Laniado | |
| 2017/0252014 A1 | 9/2017 | Siller Gonzalez et al. | |
| 2017/0252202 A9 | 9/2017 | Sanchez et al. | |
| 2017/0266031 A1* | 9/2017 | Sanchez | A61F 5/443 |
| 2017/0266658 A1 | 9/2017 | Bruno et al. | |
| 2017/0281399 A1* | 10/2017 | VanMiddendorp | A61M 1/80 |
| 2017/0281419 A1 | 10/2017 | Pintado | |
| 2017/0312116 A1 | 11/2017 | Laniado | |
| 2017/0325788 A1 | 11/2017 | Ealovega et al. | |
| 2017/0333244 A1 | 11/2017 | Laniado | |
| 2017/0348139 A1* | 12/2017 | Newton | A61F 5/4404 |
| 2017/0354532 A1 | 12/2017 | Holt | |
| 2017/0354551 A1 | 12/2017 | Gawley et al. | |
| 2017/0367873 A1 | 12/2017 | Grannum | |
| 2018/0002075 A1 | 1/2018 | Lee | |
| 2018/0008451 A1 | 1/2018 | Stroebech | |
| 2018/0008804 A1 | 1/2018 | Laniado | |
| 2018/0021218 A1 | 1/2018 | Brosch et al. | |
| 2018/0028349 A1* | 2/2018 | Newton | A61M 1/71 |
| 2018/0037384 A1 | 2/2018 | Archeny et al. | |
| 2018/0049910 A1 | 2/2018 | Newton | |
| 2018/0064572 A1 | 3/2018 | Wiltshire | |
| 2018/0104131 A1 | 4/2018 | Killian | |
| 2018/0127187 A1 | 5/2018 | Sewell | |
| 2018/0193215 A1 | 7/2018 | Davies et al. | |
| 2018/0200101 A1 | 7/2018 | Su | |
| 2018/0221216 A1 | 8/2018 | Benz et al. | |
| 2018/0228642 A1* | 8/2018 | Davis | A61B 5/208 |
| 2018/0256384 A1 | 9/2018 | Kasirye | |
| 2018/0271694 A1 | 9/2018 | Fernandez et al. | |
| 2018/0317892 A1 | 11/2018 | Catlin | |
| 2018/0325748 A1 | 11/2018 | Sharma et al. | |
| 2019/0001030 A1 | 1/2019 | Braga et al. | |
| 2019/0021899 A1 | 1/2019 | Vlet | |
| 2019/0038451 A1* | 2/2019 | Harvie | A61F 5/441 |
| 2019/0046102 A1 | 2/2019 | Kushnir et al. | |
| 2019/0059938 A1 | 2/2019 | Holsten | |
| 2019/0091059 A1 | 3/2019 | Gabriel | |
| 2019/0100362 A1 | 4/2019 | Meyers et al. | |
| 2019/0133126 A1 | 5/2019 | Modak et al. | |
| 2019/0133814 A1 | 5/2019 | Tammen et al. | |
| 2019/0142624 A1* | 5/2019 | Sanchez | A61F 5/453 |
| | | | 604/319 |
| 2019/0224036 A1* | 7/2019 | Sanchez | A61F 5/455 |
| 2019/0226189 A1 | 7/2019 | Braxton | |
| 2019/0240079 A1 | 8/2019 | Tuli | |

(56) References Cited

U.S. PATENT DOCUMENTS

| | | |
|---|---|---|
| 2019/0247222 A1 | 8/2019 | Ecklund et al. |
| 2019/0247223 A1 | 8/2019 | Brun et al. |
| 2019/0247623 A1* | 8/2019 | Helm ................... A61F 13/023 |
| 2019/0282391 A1 | 9/2019 | Johannes et al. |
| 2019/0314189 A1 | 10/2019 | Acosta |
| 2019/0314190 A1* | 10/2019 | Sanchez .................. A61F 5/443 |
| 2019/0321587 A1 | 10/2019 | Mcmenamin et al. |
| 2019/0344934 A1 | 11/2019 | Faerber et al. |
| 2019/0365303 A1 | 12/2019 | Bullington et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1* | 2/2020 | Godinez ................. A61F 5/455 |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0187918 A1 | 6/2020 | Wiygul |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1* | 12/2020 | Staali ....................... A61M 1/71 |
| 2020/0375810 A1 | 12/2020 | Carlin et al. |
| 2020/0384242 A1 | 12/2020 | Havard et al. |
| 2020/0385179 A1 | 12/2020 | Mccourt |
| 2020/0390591 A1* | 12/2020 | Glithero ................ A61F 5/4401 |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1* | 3/2021 | Davis ..................... A61B 5/208 |
| 2021/0061523 A1 | 3/2021 | Bytheway |
| 2021/0069005 A1* | 3/2021 | Sanchez ................ A61F 5/4404 |
| 2021/0069008 A1* | 3/2021 | Blabas .................... A61F 5/455 |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0186744 A1 | 6/2021 | Spector |
| 2021/0211568 A1 | 7/2021 | Zhou et al. |
| 2021/0212865 A1 | 7/2021 | Wallajapet et al. |
| 2021/0220162 A1* | 7/2021 | Jamison .................. A61F 5/453 |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1* | 7/2021 | Hughett ................. A61F 5/451 |
| 2021/0229877 A1 | 7/2021 | Ragias et al. |
| 2021/0236323 A1* | 8/2021 | Austermann ........... A61F 5/455 |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1* | 9/2021 | Sanchez ................ A61F 5/4404 |
| 2021/0275344 A1 | 9/2021 | Wing |
| 2021/0290454 A1 | 9/2021 | Yamada |
| 2021/0315726 A1 | 10/2021 | Lin |
| 2021/0315727 A1 | 10/2021 | Jiang |
| 2021/0353449 A1 | 11/2021 | Sharma et al. |
| 2021/0353450 A1* | 11/2021 | Sharma ................. A61F 5/4408 |
| 2021/0361469 A1 | 11/2021 | Liu et al. |
| 2021/0369495 A1* | 12/2021 | Cheng ..................... A61F 5/451 |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0026546 A1 | 1/2022 | Aono et al. |
| 2022/0031290 A1 | 2/2022 | Weed |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062025 A1 | 3/2022 | Shields et al. |
| 2022/0062027 A1 | 3/2022 | Mitchell et al. |
| 2022/0062028 A1* | 3/2022 | Mitchell ............... A61F 5/4405 |
| 2022/0062029 A1* | 3/2022 | Johannes .............. A61F 5/4401 |
| 2022/0066825 A1 | 3/2022 | Saraf et al. |
| 2022/0071811 A1* | 3/2022 | Cheng ................... A61F 5/4404 |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1* | 4/2022 | Meyer ..................... A61F 5/455 |
| 2022/0117775 A1* | 4/2022 | Jones ................. A61L 26/0009 |
| 2022/0118165 A1 | 4/2022 | Knapp et al. |
| 2022/0133524 A1* | 5/2022 | Davis ..................... A61M 1/60 604/319 |
| 2022/0151817 A1* | 5/2022 | Mann ...................... A61F 5/451 |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1* | 8/2022 | Johannes ................ A61F 5/453 |
| 2022/0265460 A1 | 8/2022 | Coker |
| 2022/0265462 A1* | 8/2022 | Alder .................... A61F 5/4404 |
| 2022/0270711 A1 | 8/2022 | Feala et al. |
| 2022/0273482 A1 | 9/2022 | Johannes et al. |
| 2022/0280357 A1* | 9/2022 | Jagannathan ........... A61F 13/84 |
| 2022/0280710 A1 | 9/2022 | Agrawal et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1* | 10/2022 | Austermann ........... A61F 5/455 |
| 2022/0313474 A1 | 10/2022 | Kriscovich et al. |
| 2022/0331170 A1 | 10/2022 | Erdem et al. |
| 2022/0339023 A1 | 10/2022 | Davis et al. |
| 2022/0339024 A1 | 10/2022 | Johannes et al. |
| 2022/0354685 A1* | 11/2022 | Davis ..................... A61B 5/208 |
| 2022/0362049 A1 | 11/2022 | Austermann et al. |
| 2022/0370231 A1 | 11/2022 | Wang et al. |
| 2022/0370234 A1* | 11/2022 | Hughett ................. A61F 5/4405 |
| 2022/0370235 A1* | 11/2022 | Johannes ................ A61F 5/453 |
| 2022/0370237 A1 | 11/2022 | Parmar et al. |

(56) References Cited

U.S. PATENT DOCUMENTS

| | | | |
|---|---|---|---|
| 2022/0387001 A1* | 12/2022 | Askenazi | A61F 5/455 |
| 2022/0387693 A1 | 12/2022 | Bannwart et al. | |
| 2022/0395390 A1 | 12/2022 | Brooks | |
| 2022/0395391 A1* | 12/2022 | Saunders | A61F 5/4404 |
| 2022/0401252 A1 | 12/2022 | Warren | |
| 2022/0409419 A1 | 12/2022 | Garvey et al. | |
| 2022/0409422 A1 | 12/2022 | Schneider et al. | |
| 2023/0018845 A1 | 1/2023 | Lee | |
| 2023/0020563 A1* | 1/2023 | Sharma | A61F 5/443 |
| 2023/0031640 A1 | 2/2023 | Hughett et al. | |
| 2023/0037159 A1 | 2/2023 | Brennan et al. | |
| 2023/0049924 A1* | 2/2023 | Johannes | A61F 5/442 |
| 2023/0052238 A1 | 2/2023 | Oluwasogo | |
| 2023/0062994 A1 | 3/2023 | Ecklund et al. | |
| 2023/0070347 A1 | 3/2023 | Watson et al. | |
| 2023/0073708 A1 | 3/2023 | Xu et al. | |
| 2023/0089032 A1* | 3/2023 | Hughett | A61F 5/4401 |
| | | | 604/319 |
| 2023/0091118 A1 | 3/2023 | Watson | |
| 2023/0099821 A1 | 3/2023 | Radl et al. | |
| 2023/0099991 A1 | 3/2023 | Bianchi et al. | |
| 2023/0105001 A1 | 4/2023 | Whittome et al. | |
| 2023/0110577 A1 | 4/2023 | Choi | |
| 2023/0138269 A1* | 5/2023 | Abdelal | A61F 5/451 |
| | | | 604/347 |
| 2023/0145365 A1 | 5/2023 | Martin et al. | |
| 2023/0155253 A1 | 5/2023 | Mn et al. | |
| 2023/0190511 A1 | 6/2023 | Sharma et al. | |
| 2023/0210504 A1 | 7/2023 | Kuroda et al. | |
| 2023/0210685 A1 | 7/2023 | Fallows et al. | |
| 2023/0218426 A1 | 7/2023 | Hughett | |
| 2023/0240884 A1 | 8/2023 | Davis et al. | |
| 2023/0248562 A1 | 8/2023 | Sanchez et al. | |
| 2023/0248564 A1 | 8/2023 | Mann et al. | |
| 2023/0255812 A1 | 8/2023 | Sanchez et al. | |
| 2023/0255813 A1 | 8/2023 | Sanchez et al. | |
| 2023/0255815 A1 | 8/2023 | Newton | |
| 2023/0263650 A1 | 8/2023 | Sanchez et al. | |
| 2023/0263655 A1 | 8/2023 | Johannes et al. | |
| 2023/0277360 A1 | 9/2023 | Lambert et al. | |
| 2023/0277362 A1* | 9/2023 | Davis | A61B 5/208 |
| | | | 604/319 |
| 2023/0285178 A1 | 9/2023 | Sanchez et al. | |
| 2023/0293339 A1 | 9/2023 | James | |
| 2023/0301846 A1 | 9/2023 | Greenwood | |
| 2023/0355423 A1 | 11/2023 | Stevenson et al. | |
| 2023/0389900 A1 | 12/2023 | Xie et al. | |
| 2023/0404791 A1 | 12/2023 | Ecklund et al. | |
| 2024/0008444 A1 | 1/2024 | Su et al. | |
| 2024/0009023 A1 | 1/2024 | Johannes et al. | |
| 2024/0014170 A1 | 1/2024 | Scott | |
| 2024/0033148 A1 | 2/2024 | Gordon et al. | |
| 2024/0041638 A1 | 2/2024 | Johannes et al. | |
| 2024/0058160 A1 | 2/2024 | Young Joyner et al. | |
| 2024/0058161 A1 | 2/2024 | Ulreich et al. | |
| 2024/0058520 A1 | 2/2024 | Yin et al. | |
| 2024/0065881 A1 | 2/2024 | Kuroda et al. | |
| 2024/0082044 A1 | 3/2024 | Nguyen et al. | |
| 2024/0099874 A1 | 3/2024 | Sanchez et al. | |
| 2024/0108268 A1 | 4/2024 | Woodard et al. | |
| 2024/0110318 A1 | 4/2024 | Bendt et al. | |
| 2024/0122773 A1 | 4/2024 | Nguyen et al. | |
| 2024/0123134 A1 | 4/2024 | Kharkar et al. | |
| 2024/0130885 A1 | 4/2024 | Young Joyner et al. | |
| 2024/0148539 A1 | 5/2024 | Austermann et al. | |
| 2024/0156633 A1 | 5/2024 | Fallows et al. | |
| 2024/0164935 A1 | 5/2024 | Newton | |
| 2024/0252343 A1 | 8/2024 | Voda | |
| 2024/0261131 A1 | 8/2024 | Garvey et al. | |
| 2024/0268986 A1 | 8/2024 | Barnes et al. | |
| 2024/0268989 A1 | 8/2024 | Martin et al. | |
| 2024/0268991 A1 | 8/2024 | Davis | |
| 2024/0269027 A1 | 8/2024 | Tourchak et al. | |
| 2024/0285425 A1 | 8/2024 | Donohoe et al. | |
| 2024/0325190 A1 | 10/2024 | Minchew et al. | |
| 2024/0358539 A1 | 10/2024 | Gallup | |
| 2024/0358542 A1 | 10/2024 | Richardson et al. | |
| 2024/0374414 A1 | 11/2024 | Richardson et al. | |
| 2025/0009552 A1 | 1/2025 | Blabas et al. | |
| 2025/0073055 A1 | 3/2025 | Ecklund et al. | |
| 2025/0107920 A1 | 4/2025 | Fallows et al. | |
| 2025/0107921 A1 | 4/2025 | Sanchez et al. | |

FOREIGN PATENT DOCUMENTS

| | | |
|---|---|---|
| AU | 2022349367 A1 | 4/2024 |
| CA | 2165286 C | 9/1999 |
| CA | 2335223 A1 | 1/2000 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CA | 3144181 A1 | 1/2021 |
| CA | 3188651 A1 | 7/2023 |
| CN | 2269203 Y | 12/1997 |
| CN | 1332620 A | 1/2002 |
| CN | 1434693 A | 8/2003 |
| CN | 1533755 A | 10/2004 |
| CN | 1579348 A | 2/2005 |
| CN | 1602825 A | 4/2005 |
| CN | 1638708 A | 7/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 111991136 A | 11/2020 |
| CN | 112022488 A | 12/2020 |
| CN | 212234893 U | 12/2020 |
| CN | 212466312 U | 2/2021 |
| CN | 112566550 A | 3/2021 |
| CN | 112603184 A | 4/2021 |
| CN | 213490035 U | 6/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DE | 102018118570 A1 | 2/2020 |
| DE | 102020121462 B3 | 1/2022 |
| DK | 9600118 | 11/1996 |
| EP | 0032138 A2 | 7/1981 |
| EP | 0066070 B1 | 12/1982 |

(56)  References Cited

FOREIGN PATENT DOCUMENTS

| | | | |
|---|---|---|---|
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4218702 | A1 | 8/2023 |
| EP | 4382082 | A2 | 6/2024 |
| EP | 4445881 | A2 | 10/2024 |
| EP | 4464288 | A2 | 11/2024 |
| EP | 4527361 | A2 | 3/2025 |
| FR | 2826704 | A1 | 1/2003 |
| GB | 871820 | A | 7/1961 |
| GB | 0873045 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H08117271 | A | 5/1996 |
| JP | 2686634 | B2 | 12/1997 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 2/2006 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 2010536439 | A | 12/2010 |
| JP | 2011500225 | A | 1/2011 |
| JP | 2011030962 | A | 2/2011 |
| JP | 4640772 | B2 | 3/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |

(56) References Cited

FOREIGN PATENT DOCUMENTS

| | | | |
|---|---|---|---|
| JP | 2011202664 A | 10/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2015221390 A | 12/2015 |
| JP | 2016521191 A | 7/2016 |
| JP | 2017014698 A | 1/2017 |
| JP | 3208707 U | 2/2017 |
| JP | 3209321 U | 3/2017 |
| JP | 2017070400 A | 4/2017 |
| JP | 2017512603 A | 5/2017 |
| JP | 2017127596 A | 7/2017 |
| JP | 2017201272 A | 11/2017 |
| JP | 2019010375 A | 1/2019 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020510464 A | 4/2020 |
| JP | 2020520775 A | 7/2020 |
| JP | 2020124425 A | 8/2020 |
| JP | 2021007472 A | 1/2021 |
| JP | 2021041145 A | 3/2021 |
| JP | 2021074491 A | 5/2021 |
| JP | 2021120686 A | 8/2021 |
| JP | 2021520952 A | 8/2021 |
| JP | 2021522009 A | 8/2021 |
| JP | 2021522013 A | 8/2021 |
| JP | 2021522019 A | 8/2021 |
| JP | 7129493 B2 | 8/2022 |
| JP | 2022554252 A | 12/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090072069 A | 7/2009 |
| KR | 20090104426 A | 10/2009 |
| KR | 20090110359 A | 10/2009 |
| KR | 20120005922 A | 1/2012 |
| KR | 20140039485 A | 4/2014 |
| KR | 101432639 B1 | 8/2014 |
| KR | 20180106659 A | 10/2018 |
| KR | 20180108774 A | 10/2018 |
| KR | 20230034343 A | 3/2023 |
| PT | 2068717 E | 6/2013 |
| SE | 505542 C2 | 9/1997 |
| TW | 408207 B | 10/2000 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9416914 A1 | 8/1994 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03015671 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005060558 A2 | 7/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012020506 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |

(56) References Cited

FOREIGN PATENT DOCUMENTS

| | | | |
|---|---|---|---|
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017001846 A1 | 1/2017 |
| WO | 2017075226 A1 | 5/2017 |
| WO | 2017100511 A1 | 6/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018150263 A1 | 8/2018 |
| WO | 2018150268 A1 | 8/2018 |
| WO | 2018152156 A1 | 8/2018 |
| WO | WO-2018144463 A1 * | 8/2018 | ........... A61F 5/4405 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020033752 A1 | 2/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016056 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022029662 A1 | 2/2022 |
| WO | 2022031943 A1 | 2/2022 |
| WO | 2022035745 A1 | 2/2022 |
| WO | 2022051220 A1 | 3/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150290 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022173803 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2022251184 A1 | 12/2022 |
| WO | 2022251425 A1 | 12/2022 |
| WO | 2022271783 A1 | 12/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023018656 A1 | 2/2023 |
| WO | 2023018657 A1 | 2/2023 |
| WO | 2023023777 A1 | 3/2023 |
| WO | 2023034139 A1 | 3/2023 |
| WO | 2023034453 A1 | 3/2023 |
| WO | 2023038945 A1 | 3/2023 |

(56) References Cited

FOREIGN PATENT DOCUMENTS

| WO | 2023038950 A1 | 3/2023 |
|----|---------------|--------|
| WO | 2023049109 A1 | 3/2023 |
| WO | 2023049156 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023163725 A1 | 8/2023 |
| WO | 2023191764 A1 | 10/2023 |
| WO | 2023244238 A1 | 12/2023 |
| WO | 2024043871 A1 | 2/2024 |
| WO | 2024058788 A1 | 3/2024 |
| WO | 2024253655 A1 | 12/2024 |
| WO | 2025034959 A1 | 2/2025 |
| WO | 2025038087 A1 | 2/2025 |
| WO | 2025038088 A1 | 2/2025 |
| WO | 2025071622 A1 | 4/2025 |
| WO | 2025179267 A1 | 8/2025 |

OTHER PUBLICATIONS

Advisory Action for U.S. Appl. No. 16/478,180 mailed Sep. 21, 2022.
International Search Report and Written Opinion from International Application No. PCT/US2021/039866 mailed Oct. 7, 2021.
International Search Report and Written Opinion from International Application No. PCT/US2022/015492 mailed Apr. 26, 2022.
Notice of Allowance for U.S. Appl. No. 16/905,400 mailed Aug. 17, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 62/991,754, filed Mar. 19, 2020.
U.S. Appl. No. 63/241,328, filed Sep. 7, 2021.
Advisory Action for U.S. Appl. No. 16/452,258 mailed Oct. 26, 2022.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.

International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/044107 mailed Dec. 23, 2022.
Issue Notification for U.S. Appl. No. 16/905,400 mailed Nov. 30, 2022.
Non-Final Office Action for U.S. Appl. No. 16/478,180 mailed Dec. 20, 2022.
Non-Final Office Action for U.S. Appl. No. 17/051,550 mailed Dec. 15, 2022.
Non-Final Office Action for U.S. Appl. No. 17/451,345 mailed Dec. 7, 2022.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/461,036 mailed Oct. 6, 2022.
U.S. Appl. No. 17/930,238 filled Sep. 7, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 18/003,029, filed Dec. 22, 2022.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.

(56)     References Cited

OTHER PUBLICATIONS

Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.

International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.

(56)     References Cited

OTHER PUBLICATIONS

International Search Report and Written Opinion from International Application No. PCT/US2021/062440 mailed Mar. 28, 2022.

International Search Report and Written Opinion from International Application No. PCT/US2022/011108 mailed Apr. 22, 2022.

International Search Report and Written Opinion from International Application No. PCT/US2022/011281 mailed Apr. 25, 2022.

International Search Report and Written Opinion from International Application No. PCT/US2022/011419 mailed Jun. 7, 2022.

International Search Report and Written Opinion from International Application No. PCT/US2022/011421 mailed Jun. 13, 2022.

International Search Report and Written Opinion from International Application No. PCT/US2022/012794 mailed May 3, 2022.

International Search Report and Written Opinion from International Application No. PCT/US2022/015471 mailed May 16, 2022.

International Search Report and Written Opinion from International Application No. PCT/US2022/016942 mailed Jun. 8, 2022.

International Search Report and Written Opinion from International Application No. PCT/US2022/018170 mailed May 31, 2022.

International Search Report and Written Opinion from International Application No. PCT/US2022/019254 mailed Jun. 7, 2022.

International Search Report and Written Opinion from International Application No. PCT/US2022/019480 mailed Jun. 13, 2022.

International Search Report and Written Opinion from International Application No. PCT/US2022/021103 mailed Jun. 23, 2022.

Issue Notification for U.S. Appl. No. 14/952,591 mailed Jul. 28, 2021.

Issue Notification for U.S. Appl. No. 15/171,968 mailed Mar. 3, 2021.

Issue Notification for U.S. Appl. No. 15/221,106 mailed Jul. 24, 2019.

Issue Notification for U.S. Appl. No. 15/238,427 mailed Jul. 24, 2019.

Issue Notification for U.S. Appl. No. 15/260,103 mailed Aug. 7, 2019.

Issue Notification for U.S. Appl. No. 15/611,587 mailed Feb. 20, 2019.

Issue Notification for U.S. Appl. No. 15/612,325 mailed Mar. 24, 2021.

Issue Notification for U.S. Appl. No. 17/088,272 mailed Jun. 15, 2022.

Issue Notification for U.S. Appl. No. 17/330,657 mailed Jun. 22, 2022.

Issue Notification for U.S. Appl. No. 29/624,661 mailed Aug. 4, 2021.

Non-Final Office Action for U.S. Appl. No. 14/592,591 mailed Mar. 20, 2020.

Non-Final Office Action for U.S. Appl. No. 14/722,613 mailed Jun. 13, 2019.

Non-Final Office Action for U.S. Appl. No. 14/947,759 mailed Mar. 17, 2016.

Non-Final Office Action for U.S. Appl. No. 14/952,591 mailed Aug. 1, 2017.

Non-Final Office Action for U.S. Appl. No. 14/952,591 mailed Mar. 20, 2020.

Non-Final Office Action for U.S. Appl. No. 14/952,591 mailed Mar. 21, 2019.

Non-Final Office Action for U.S. Appl. No. 14/952,591 mailed Sep. 28, 2018.

Non-Final Office Action for U.S. Appl. No. 15/171,968 mailed May 11, 2020.

Non-Final Office Action for U.S. Appl. No. 15/171,968 mailed Aug. 20, 2019.

Non-Final Office Action for U.S. Appl. No. 15/171,968 mailed Jun. 12, 2018.

Non-Final Office Action for U.S. Appl. No. 15/221,106 mailed Jun. 5, 2018.

Non-Final Office Action for U.S. Appl. No. 15/238,427 mailed Aug. 8, 2018.

Non-Final Office Action for U.S. Appl. No. 15/260,103 mailed Sep. 26, 2018.

Non-Final Office Action for U.S. Appl. No. 15/611,587 mailed Dec. 29, 2017.

Non-Final Office Action for U.S. Appl. No. 15/611,587 mailed Jul. 13, 2018.

Non-Final Office Action for U.S. Appl. No. 15/612,325 mailed Mar. 19, 2020.

Non-Final Office Action for U.S. Appl. No. 16/245,726 mailed Jan. 21, 2022.

Non-Final Office Action for U.S. Appl. No. 16/369,676 mailed Mar. 31, 2022.

Non-Final Office Action for U.S. Appl. No. 16/433,773 mailed Apr. 21, 2022.

Non-Final Office Action for U.S. Appl. No. 16/449,039 mailed Dec. 8, 2021.

Non-Final Office Action for U.S. Appl. No. 16/452,145 mailed Sep. 28, 2021.

Non-Final Office Action for U.S. Appl. No. 16/452,258 mailed Sep. 28, 2021.

Non-Final Office Action for U.S. Appl. No. 16/478,180 mailed Oct. 22, 2021.

Non-Final Office Action for U.S. Appl. No. 16/899,956 mailed Oct. 16, 2020.

Non-Final Office Action for U.S. Appl. No. 16/899,956 mailed Sep. 2, 2021.

Non-Final Office Action for U.S. Appl. No. 16/904,868 mailed Nov. 25, 2020.

Non-Final Office Action for U.S. Appl. No. 16/904,868 mailed Oct. 5, 2021.

Non-Final Office Action for U.S. Appl. No. 16/905,400 mailed Apr. 27, 2022.

Non-Final Office Action for U.S. Appl. No. 16/905,400 mailed Dec. 2, 2020.

Non-Final Office Action for U.S. Appl. No. 16/905,400 mailed Jul. 22, 2021.

Non-Final Office Action for U.S. Appl. No. 17/088,272 mailed Jan. 25, 2021.

Non-Final Office Action for U.S. Appl. No. 17/330,657 mailed Aug. 11, 2021.

Non-Final Office Action for U.S. Appl. No. 17/662,700 mailed Jul. 22, 2022.

Non-Final Office Action for U.S. Appl. No. 29/624,661 mailed Jul. 18, 2019.

Non-Final Office Action for U.S. Appl. No. 29/694,002 mailed Jun. 24, 2020.

Non-Final Office Action for U.S. Appl. No. 29/741,751 mailed Jan. 18, 2022.

Notice of Allowance for U.S. Appl. No. 14/952,591 mailed Apr. 5, 2021.

Notice of Allowance for U.S. Appl. No. 14/952,591 mailed Jul. 8, 2021.

Notice of Allowance for U.S. Appl. No. 15/171,968 mailed Feb. 16, 2021.

Notice of Allowance for U.S. Appl. No. 15/171,968 mailed Nov. 6, 2020.

Notice of Allowance for U.S. Appl. No. 15/221,106 mailed May 1, 2019.

Notice of Allowance for U.S. Appl. No. 15/238,427 mailed May 23, 2019.

Notice of Allowance for U.S. Appl. No. 15/260,103 mailed Jun. 7, 2019.

Notice of Allowance for U.S. Appl. No. 15/611,587 mailed Dec. 21, 2018.

Notice of Allowance for U.S. Appl. No. 15/612,325 mailed Feb. 19, 2021.

Notice of Allowance for U.S. Appl. No. 15/612,325 mailed Jan. 21, 2021.

Notice of Allowance for U.S. Appl. No. 16/899,956 mailed Apr. 19, 2022.

Notice of Allowance for U.S. Appl. No. 16/899,956 mailed Aug. 10, 2022.

(56) References Cited

OTHER PUBLICATIONS

Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/878,268, filed Aug. 1, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.

(56) References Cited

OTHER PUBLICATIONS

U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.

U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. No's 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.

(56)          References Cited

OTHER PUBLICATIONS

"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.

Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.

(56)            References Cited

OTHER PUBLICATIONS

Corrected Notice of Allowability for U.S. Appl. No. 17/657,474 mailed Mar. 13, 2024.

Corrected Notice of Allowability for U.S. Appl. No. 17/657,474 mailed May 14, 2024.

Final Office Action for U.S. Appl. No. 16/369,676 mailed Aug. 31, 2023.

Final Office Action for U.S. Appl. No. 16/433,773 mailed Oct. 10, 2023.

Final Office Action for U.S. Appl. No. 16/449,039 mailed Nov. 21, 2023.

Final Office Action for U.S. Appl. No. 16/452,258 mailed Dec. 21, 2023.

Final Office Action for U.S. Appl. No. 16/478,180 mailed Feb. 28, 2024.

Final Office Action for U.S. Appl. No. 16/478,180 mailed May 31, 2023.

Final Office Action for U.S. Appl. No. 16/904,868 mailed Nov. 2, 2023.

Final Office Action for U.S. Appl. No. 17/051,399 mailed Jan. 8, 2024.

Final Office Action for U.S. Appl. No. 17/051,399 mailed Mar. 9, 2023.

Final Office Action for U.S. Appl. No. 17/051,550 mailed May 23, 2023.

Final Office Action for U.S. Appl. No. 17/051,585 mailed Jul. 27, 2023.

Final Office Action for U.S. Appl. No. 17/051,585 mailed Jul. 5, 2024.

Final Office Action for U.S. Appl. No. 17/051,600 mailed Jun. 27, 2024.

Final Office Action for U.S. Appl. No. 17/179,116 mailed Oct. 31, 2023.

Final Office Action for U.S. Appl. No. 17/444,792 mailed Apr. 3, 2024.

Final Office Action for U.S. Appl. No. 17/444,792 mailed Jun. 15, 2023.

Final Office Action for U.S. Appl. No. 17/446,256 mailed Sep. 19, 2023.

Final Office Action for U.S. Appl. No. 17/446,654 mailed Jan. 31, 2024.

Final Office Action for U.S. Appl. No. 17/447,123 mailed May 14, 2024.

Final Office Action for U.S. Appl. No. 17/448,811 mailed Aug. 3, 2023.

Final Office Action for U.S. Appl. No. 17/450,864 mailed Dec. 28, 2023.

Final Office Action for U.S. Appl. No. 17/451,345 mailed Apr. 18, 2024.

Final Office Action for U.S. Appl. No. 17/451,345 mailed May 3, 2023.

Final Office Action for U.S. Appl. No. 17/451,354 mailed Oct. 30, 2023.

Final Office Action for U.S. Appl. No. 17/453,260 mailed Oct. 5, 2023.

Final Office Action for U.S. Appl. No. 17/501,591 mailed Nov. 14, 2023.

Final Office Action for U.S. Appl. No. 17/645,821 mailed Apr. 3, 2024.

Final Office Action for U.S. Appl. No. 17/646,771 mailed Dec. 21, 2023.

Final Office Action for U.S. Appl. No. 17/653,137 mailed Sep. 21, 2023.

Final Office Action for U.S. Appl. No. 17/655,464 mailed Sep. 1, 2023.

Final Office Action for U.S. Appl. No. 17/661,090 mailed Dec. 11, 2023.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 17/808,354 mailed Apr. 10, 2024.

Final Office Action for U.S. Appl. No. 18/139,523 mailed Dec. 22, 2023.

Final Office Action for U.S. Appl. No. 18/140,163 mailed Mar. 27, 2024.

Final Office Action for U.S. Appl. No. 18/140,751 mailed Jan. 17, 2024.

Final Office Action for U.S. Appl. No. 18/164,800 mailed Dec. 6, 2023.

International Search Report and Written Opinion from International Application No. PCT/US2022/039018 mailed Jan. 10, 2023.

International Search Report and Written Opinion from International Application No. PCT/US2022/039022 mailed Jan. 10, 2023.

International Search Report and Written Opinion from International Application No. PCT/US2022/039711 mailed Jan. 12, 2023.

International Search Report and Written Opinion from International Application No. PCT/US2022/041085 mailed Mar. 16, 2023.

International Search Report and Written Opinion from International Application No. PCT/US2022/041688 mailed Nov. 21, 2022.

International Search Report and Written Opinion from International Application No. PCT/US2022/042725 mailed Dec. 19, 2022.

International Search Report and Written Opinion from International Application No. PCT/US2022/043818 mailed Mar. 24, 2023.

International Search Report and Written Opinion from International Application No. PCT/US2022/044208 mailed May 8, 2023.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

International Search Report and Written Opinion from International Application No. PCT/US2022/049300 mailed Jun. 6, 2023.

International Search Report and Written Opinion from International Application No. PCT/US2022/050909 mailed Jul. 24, 2023.

International Search Report and Written Opinion from International Application No. PCT/US2023/012696 mailed Jul. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

International Search Report and Written Opinion from International Application No. PCT/US2023/025192 mailed Feb. 7, 2024.

International Search Report and Written Opinion from International Application No. PCT/US2023/025939 mailed Feb. 7, 2024.

International Search Report and Written Opinion from International Application No. PCT/US2023/030365 mailed Mar. 13, 2024.

International Search Report and Written Opinion from International Application No. PCT/US2023/030373 mailed Mar. 13, 2024.

International Search Report and Written Opinion from International Application No. PCT/US2023/031433 mailed Mar. 4, 2024.

International Search Report and Written Opinion from International Application No. PCT/US2023/031740 mailed Mar. 4, 2024.

International Search Report and Written Opinion from International Application No. PCT/US2023/036868 mailed Jun. 5, 2024.

International Search Report and Written Opinion from International Application No. PCT/US2023/075507 mailed Jun. 13, 2024.

International Search Report and Written Opinion from International Application No. PCT/US2023/077208 mailed May 10, 2024.

Issue Notification for U.S. Appl. No. 16/245,726 mailed Oct. 18, 2023.

Issue Notification for U.S. Appl. No. 16/449,039 mailed Jun. 19, 2024.

Issue Notification for U.S. Appl. No. 16/899,956 mailed Mar. 29, 2023.

Issue Notification for U.S. Appl. No. 17/051,550 mailed Mar. 13, 2024.

Issue Notification for U.S. Appl. No. 17/051,554 mailed Mar. 6, 2024.

Issue Notification for U.S. Appl. No. 17/326,980 mailed Jul. 10, 2024.

(56)  References Cited

OTHER PUBLICATIONS

Issue Notification for U.S. Appl. No. 17/448,811 mailed Jul. 3, 2024.

Issue Notification for U.S. Appl. No. 17/453,260 mailed Jul. 10, 2024.

Issue Notification for U.S. Appl. No. 17/461,036 mailed Oct. 11, 2023.

Issue Notification for U.S. Appl. No. 17/657,474 mailed Jun. 19, 2024.

Issue Notification for U.S. Appl. No. 17/663,046 mailed Dec. 20, 2023.

Issue Notification for U.S. Appl. No. 18/299,788 mailed Feb. 21, 2024.

Non-Final Office Action for U.S. Appl. No. 16/369,676 mailed Feb. 29, 2024.

Non-Final Office Action for U.S. Appl. No. 16/433,773 mailed Apr. 11, 2023.

Non-Final Office Action for U.S. Appl. No. 16/433,773 mailed Feb. 26, 2024.

Non-Final Office Action for U.S. Appl. No. 16/449,039 mailed Apr. 27, 2023.

Non-Final Office Action for U.S. Appl. No. 16/452,145 mailed Mar. 28, 2023.

Non-Final Office Action for U.S. Appl. No. 16/452,145 mailed Nov. 2, 2023.

Non-Final Office Action for U.S. Appl. No. 16/452,258 mailed Apr. 26, 2023.

Non-Final Office Action for U.S. Appl. No. 16/452,258 mailed Jun. 20, 2024.

Non-Final Office Action for U.S. Appl. No. 16/478,180 mailed Nov. 7, 2023.

Non-Final Office Action for U.S. Appl. No. 16/904,868 mailed Mar. 12, 2024.

Non-Final Office Action for U.S. Appl. No. 16/904,868 mailed Mar. 15, 2023.

Non-Final Office Action for U.S. Appl. No. 17/051,399 mailed Aug. 18, 2023.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,585 mailed Mar. 29, 2023.

Non-Final Office Action for U.S. Appl. No. 17/051,600 mailed Jan. 17, 2024.

Non-Final Office Action for U.S. Appl. No. 17/179,116 mailed Feb. 26, 2024.

Non-Final Office Action for U.S. Appl. No. 17/179,116 mailed Mar. 24, 2023.

Non-Final Office Action for U.S. Appl. No. 17/326,980 mailed Jul. 11, 2023.

Non-Final Office Action for U.S. Appl. No. 17/378,015 mailed Jul. 5, 2024.

Non-Final Office Action for U.S. Appl. No. 17/444,792 mailed Feb. 10, 2023.

Non-Final Office Action for U.S. Appl. No. 17/444,792 mailed Nov. 17, 2023.

Non-Final Office Action for U.S. Appl. No. 17/446,256 mailed Apr. 13, 2023.

Non-Final Office Action for U.S. Appl. No. 17/446,256 mailed Feb. 13, 2024.

Non-Final Office Action for U.S. Appl. No. 17/446,654 mailed Jun. 25, 2024.

Non-Final Office Action for U.S. Appl. No. 17/446,654 mailed Sep. 8, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/450,864 mailed May 29, 2024.

Non-Final Office Action for U.S. Appl. No. 17/451,345 mailed Jan. 17, 2024.

Non-Final Office Action for U.S. Appl. No. 17/451,354 mailed Apr. 4, 2024.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/453,560 mailed Oct. 16, 2023.

Non-Final Office Action for U.S. Appl. No. 17/501,591 mailed Apr. 25, 2023.

Non-Final Office Action for U.S. Appl. No. 17/595,747 mailed Jun. 7, 2024.

Non-Final Office Action for U.S. Appl. No. 17/597,673 mailed Mar. 20, 2024.

Non-Final Office Action for U.S. Appl. No. 17/645,821 mailed Oct. 25, 2023.

Non-Final Office Action for U.S. Appl. No. 17/646,771 mailed Apr. 24, 2024.

Non-Final Office Action for U.S. Appl. No. 17/646,771 mailed Jul. 5, 2023.

Non-Final Office Action for U.S. Appl. No. 17/653,137 mailed Apr. 7, 2023.

Non-Final Office Action for U.S. Appl. No. 17/653,137 mailed Jan. 18, 2024.

Non-Final Office Action for U.S. Appl. No. 17/653,920 mailed Mar. 15, 2024.

Non-Final Office Action for U.S. Appl. No. 17/655,464 mailed Mar. 14, 2023.

Non-Final Office Action for U.S. Appl. No. 17/655,464 mailed Mar. 26, 2024.

Non-Final Office Action for U.S. Appl. No. 17/657,474 mailed Sep. 12, 2023.

Non-Final Office Action for U.S. Appl. No. 17/661,090 mailed Jul. 6, 2023.

Non-Final Office Action for U.S. Appl. No. 17/661,090 mailed May 22, 2024.

Non-Final Office Action for U.S. Appl. No. 17/663,330 mailed Jul. 1, 2024.

Non-Final Office Action for U.S. Appl. No. 17/663,330 mailed Jun. 29, 2023.

Non-Final Office Action for U.S. Appl. No. 17/664,487 mailed Jun. 17, 2024.

Non-Final Office Action for U.S. Appl. No. 17/664,487 mailed Jun. 8, 2023.

Non-Final Office Action for U.S. Appl. No. 17/664,914 mailed Jan. 31, 2024.

Non-Final Office Action for U.S. Appl. No. 17/808,354 mailed Nov. 28, 2023.

Non-Final Office Action for U.S. Appl. No. 18/003,029 mailed Mar. 26, 2024.

Non-Final Office Action for U.S. Appl. No. 18/134,857 mailed Jan. 25, 2024.

Non-Final Office Action for U.S. Appl. No. 18/139,523 mailed Aug. 17, 2023.

Non-Final Office Action for U.S. Appl. No. 18/140,163 mailed Nov. 9, 2023.

Non-Final Office Action for U.S. Appl. No. 18/140,751 mailed Jun. 21, 2024.

Non-Final Office Action for U.S. Appl. No. 18/140,751 mailed Sep. 14, 2023.

Non-Final Office Action for U.S. Appl. No. 18/164,800 mailed Mar. 22, 2024.

Non-Final Office Action for U.S. Appl. No. 18/198,464 mailed Dec. 7, 2023.

(56) References Cited

OTHER PUBLICATIONS

Non-Final Office Action for U.S. Appl. No. 18/389,009 mailed May 24, 2024.
Notice of Allowance for U.S. Appl. No. 16/245,726 mailed Jul. 6, 2023.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Jun. 12, 2024.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/527,769 mailed Jun. 17, 2024.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.

Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.

(56)         References Cited

OTHER PUBLICATIONS

*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers. com/textile-resources/synthetic-fibers/polypropylene-fiber/ polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Oblong", Cambridge Dictionary, https://dictionary.cambridge.org/ dictionary/english/oblong, 2024, 1 page.
"Revised AMXDmax Advanced Mission Extender Device User & Maintenance Guide", Omni Medical Systems, Oct. 8, 2019, 52 pages.
Britannica, "Polyolefin", Britannica Online Encyclopedia, T. Editors of Encyclopaedia, https://www.britannica.com/science/ polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution for an Awkward—But Serious—Subject", http:// www.aero-news.net/index.cfm?do=main.textpost&id=69ae2bb1-838b-4098-a7b5-7flbb2505688 last accessed Feb. 8, 2021.
Wikipedia Article, "Decibel", https://web.archive.org/web/ 2020041521917/https://en.wikipedia/org/wiki/Decibel last accessed Mar. 11, 2024, 21 pages.
Wikipedia Article, "Fiberglass", https://web.archive.org.web/ 20200309194847/https://en.wikipedia.org/wiki/Fiberglass last accessed Mar. 11, 2024.
Wikipedia Article, "Zylinder (Geometrie)", https://de.wikipedia.org/ w/index.php?title=Zylinder (Geometrie)&oldid=154862081, version of Jun. 1, 2016, 7 pages.
Advisory Action for U.S. Appl. No. 17/051,585 mailed Oct. 8, 2024.
Advisory Action for U.S. Appl. No. 17/446,256 mailed Nov. 19, 2024.
Advisory Action for U.S. Appl. No. 17/446,654 mailed Feb. 28, 2025.
Advisory Action for U.S. Appl. No. 17/595,747 mailed Mar. 17, 2025.
Advisory Action for U.S. Appl. No. 17/597,673 mailed Jan. 7, 2025.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/655,464 mailed Feb. 25, 2025.
Advisory Action for U.S. Appl. No. 18/003,029 mailed Jan. 8, 2025.

Advisory Action for U.S. Appl. No. 18/134,857 mailed Oct. 23, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 17/051,585 mailed Mar. 26, 2025.

(56)  References Cited

OTHER PUBLICATIONS

Issue Notification for U.S. Appl. No. 17/179,116 mailed Dec. 25, 2024.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/646,771 mailed Mar. 19, 2025.
Issue Notification for U.S. Appl. No. 17/661,090 mailed Feb. 5, 2025.
Issue Notification for U.S. Appl. No. 17/662,700 mailed Oct. 23, 2024.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/433,773 mailed Feb. 28, 2025.
Non-Final Office Action for U.S. Appl. No. 16/478,180 mailed Aug. 7, 2024.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/451,345 mailed Jul. 25, 2024.
Non-Final Office Action for U.S. Appl. No. 17/451,354 mailed Mar. 19, 2025.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/645,821 mailed Sep. 6, 2024.
Non-Final Office Action for U.S. Appl. No. 17/653,137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/749,340 mailed Aug. 14, 2024.
Non-Final Office Action for U.S. Appl. No. 17/754,736 mailed Mar. 31, 2025.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/808,354 mailed Dec. 13, 2024.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/996,064 mailed Mar. 6, 2025.
Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/444,792 mailed Mar. 28, 2025.
Notice of Allowance for U.S. Appl. No. 17/447,123 mailed Jul. 26, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 17/758,316 mailed Mar. 24, 2025.

(56) References Cited

OTHER PUBLICATIONS

Notice of Allowance for U.S. Appl. No. 17/996,155 mailed Mar. 11, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
U.S. Appl. No. 15/611,587, filed Jun. 1, 2017.
U.S. Appl. No. 17/013,822, filed Sep. 7, 2020.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 63/564,696, filed Mar. 13, 2024.

U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
"Surface Energy Data for Cellulose acetate, CAS # 9004-35-7", Diviersified Enterprises, 2009, 1 page.
"TUBE Definition & Meaning" Merriam Webster Dictionary, 2025, <https://www.merriam-webster.com/dictionary/tube>.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/446,256 mailed Nov. 6, 2025.
Advisory Action for U.S. Appl. No. 17/451,345 mailed May 13, 2025.
Advisory Action for U.S. Appl. No. 17/653,314 mailed Apr. 8, 2025.
Advisory Action for U.S. Appl. No. 17/664,487 mailed Apr. 24, 2025.
Advisory Action for U.S. Appl. No. 17/757,311 mailed Jul. 2, 2025.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/260,122 mailed Aug. 11, 2025.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/808,354 mailed Jun. 13, 2025.
Final Office Action for U.S. Appl. No. 17/907,125 mailed Apr. 30, 2025.
Final Office Action for U.S. Appl. No. 18/003,029 mailed Nov. 26, 2025.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/265,736 mailed Dec. 1, 2025.

(56) References Cited

OTHER PUBLICATIONS

International Search Report and Written Opinion from International Application No. PCT/US2023/036875 mailed May 31, 2024.

International Search Report and Written Opinion from International Application No. PCT/US2023/077205 mailed Jul. 19, 2024.

International Search Report and Written Opinion from International Application No. PCT/US2024/058598 mailed Mar. 28, 2025.

International Search Report and Written Opinion from International Application No. PCT/US2025/018907 mailed May 16, 2025.

International Search Report and Written Opinion from International Application No. PCT/US2025/018909 mailed May 20, 2025.

International Search Report and Written Opinion from International Application No. PCT/US2025/018913 mailed Jun. 18, 2025.

Issue Notification for U.S. Appl. No. 16/904,868 mailed Apr. 30, 2025.

Issue Notification for U.S. Appl. No. 17/444,792 mailed Jun. 25, 2025.

Issue Notification for U.S. Appl. No. 17/597,673 mailed Jun. 4, 2025.

Issue Notification for U.S. Appl. No. 17/653,920 mailed Oct. 22, 2025.

Issue Notification for U.S. Appl. No. 17/749,340 mailed May 28, 2025.

Issue Notification for U.S. Appl. No. 17/755,236 mailed Oct. 29, 2025.

Issue Notification for U.S. Appl. No. 17/758,316 mailed Jun. 25, 2025.

Issue Notification for U.S. Appl. No. 17/996,064 mailed Nov. 5, 2025.

Issue Notification for U.S. Appl. No. 17/996,155 mailed Oct. 8, 2025.

Issue Notification for U.S. Appl. No. 17/996,253 mailed Oct. 29, 2025.

Issue Notification for U.S. Appl. No. 17/996,468 mailed Nov. 26, 2025.

Issue Notification for U.S. Appl. No. 18/007,105 mailed Oct. 1, 2025.

Issue Notification for U.S. Appl. No. 18/134,857 mailed May 28, 2025.

Issue Notification for U.S. Appl. No. 18/260,122 mailed Nov. 12, 2025.

Issue Notification for U.S. Appl. No. 18/415,080 mailed Apr. 9, 2025.

Issue Notification for U.S. Appl. No. 18/584,002 mailed Apr. 16, 2025.

Non-Final Office Action for U.S. Appl. No. 16/452,258 mailed Sep. 24, 2025.

Non-Final Office Action for U.S. Appl. No. 17/378,015 mailed Dec. 12, 2025.

Non-Final Office Action for U.S. Appl. No. 17/446,256 mailed Dec. 2, 2025.

Non-Final Office Action for U.S. Appl. No. 17/446,654 mailed May 1, 2025.

Non-Final Office Action for U.S. Appl. No. 17/595,747 mailed Jun. 12, 2025.

Non-Final Office Action for U.S. Appl. No. 17/635,866 mailed Jul. 29, 2025.

Non-Final Office Action for U.S. Appl. No. 17/653,314 mailed May 8, 2025.

Non-Final Office Action for U.S. Appl. No. 17/664,487 mailed May 19, 2025.

Non-Final Office Action for U.S. Appl. No. 17/756,201 mailed Apr. 24, 2025.

Non-Final Office Action for U.S. Appl. No. 17/758,152 mailed Apr. 8, 2025.

Non-Final Office Action for U.S. Appl. No. 17/809,083 mailed Apr. 2, 2025.

Non-Final Office Action for U.S. Appl. No. 17/912,147 mailed May 29, 2025.

Non-Final Office Action for U.S. Appl. No. 17/929,887 mailed Jun. 25, 2025.

Non-Final Office Action for U.S. Appl. No. 17/930,238 mailed Jun. 30, 2025.

Non-Final Office Action for U.S. Appl. No. 17/933,590 mailed Jul. 29, 2025.

Non-Final Office Action for U.S. Appl. No. 18/003,029 mailed Apr. 18, 2025.

Non-Final Office Action for U.S. Appl. No. 18/006,807 mailed May 29, 2025.

Non-Final Office Action for U.S. Appl. No. 18/042,842 mailed May 22, 2025.

Non-Final Office Action for U.S. Appl. No. 18/043,618 mailed May 19, 2025.

Non-Final Office Action for U.S. Appl. No. 18/115,444 mailed Oct. 22, 2025.

Non-Final Office Action for U.S. Appl. No. 18/139,523 mailed Nov. 19, 2025.

Non-Final Office Action for U.S. Appl. No. 18/150,360 mailed Nov. 5, 2025.

Non-Final Office Action for U.S. Appl. No. 18/164,800 mailed Apr. 25, 2025.

Non-Final Office Action for U.S. Appl. No. 18/247,986 mailed Jun. 4, 2025.

Non-Final Office Action for U.S. Appl. No. 18/249,577 mailed Nov. 17, 2025.

Non-Final Office Action for U.S. Appl. No. 18/254,638 mailed Nov. 17, 2025.

Non-Final Office Action for U.S. Appl. No. 18/259,626 mailed Jul. 11, 2025.

Non-Final Office Action for U.S. Appl. No. 18/264,004 mailed May 15, 2025.

Non-Final Office Action for U.S. Appl. No. 18/264,278 mailed Nov. 10, 2025.

Non-Final Office Action for U.S. Appl. No. 18/265,736 mailed Jul. 1, 2025.

Non-Final Office Action for U.S. Appl. No. 18/548,152 mailed Sep. 16, 2025.

Non-Final Office Action for U.S. Appl. No. 18/553,625 mailed Oct. 2, 2025.

Non-Final Office Action for U.S. Appl. No. 18/757,964 mailed Aug. 20, 2025.

Notice of Allowance for U.S. Appl. No. 16/433,773 mailed Oct. 10, 2025.

Notice of Allowance for U.S. Appl. No. 17/051,399 mailed Nov. 17, 2025.

Notice of Allowance for U.S. Appl. No. 17/451,345 mailed Jun. 24, 2025.

Notice of Allowance for U.S. Appl. No. 17/451,354 mailed Nov. 18, 2025.

Notice of Allowance for U.S. Appl. No. 17/596,629 mailed May 27, 2025.

Notice of Allowance for U.S. Appl. No. 17/625,941 mailed Nov. 13, 2025.

Notice of Allowance for U.S. Appl. No. 17/645,821 mailed Nov. 24, 2025.

Notice of Allowance for U.S. Appl. No. 17/653,137 mailed Oct. 22, 2025.

Notice of Allowance for U.S. Appl. No. 17/653,314 mailed Oct. 20, 2025.

Notice of Allowance for U.S. Appl. No. 17/653,920 mailed Jul. 9, 2025.

Notice of Allowance for U.S. Appl. No. 17/755,236 mailed Jul. 17, 2025.

Notice of Allowance for U.S. Appl. No. 17/808,354 mailed Nov. 12, 2025.

Notice of Allowance for U.S. Appl. No. 17/878,268 mailed Oct. 15, 2025.

Notice of Allowance for U.S. Appl. No. 17/907,125 mailed Sep. 26, 2025.

Notice of Allowance for U.S. Appl. No. 17/912,147 mailed Dec. 3, 2025.

(56)          References Cited

OTHER PUBLICATIONS

Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/044,413 mailed Sep. 16, 2025.
Notice of Allowance for U.S. Appl. No. 18/260,122 mailed Jul. 30, 2025.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/294,370 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/662,216 mailed Nov. 26, 2025.
Supplemental Notice of Allowance for U.S. Appl. No. 17/597,673 mailed Apr. 10, 2025.
U.S. Appl. No. 17/596,629, filed Dec. 15, 2021.
U.S. Appl. No. 18/034,902, filed May 2, 2023.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/491,481, filed Dec. 9, 2025.

* cited by examiner

FLUID COLLECTION ASSEMBLIES INCLUDING A SKIRT

CROSS-REFERENCE TO RELATED APPLICATIONS

This application is a U.S. nationalization of PCT International Application No. PCT/US2021/015787 filed on Jan. 29, 2021, which claims priority to U.S. Provisional Patent Application No. 62/967,977 filed on Jan. 30, 2020, the disclosure of each of which is incorporated herein, in its entirety, by this reference.

BACKGROUND

A person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

Embodiments of fluid collection assemblies including a skirt, fluid collection systems including the same, and methods of using the same are disclosed herein. In an embodiment, a fluid collection assembly are disclosed. The fluid collection assembly includes a sheath. The sheath includes a proximal end defining an opening configured to receive at least a urethral opening of a penis. The sheath also includes a distal end opposite the first end defining an aperture. Additionally, the sheath includes a fluid impermeable barrier extending from the proximal end to the distal end. The fluid impermeable barrier at least partially defines a chamber extending between the opening that is configured to receive at least the urethral opening of the penis. The sheath further includes at least one porous material disposed in the chamber. The fluid collection assembly also includes a base including a skirt configured to secure the base to the individual. The skirt exhibits a flexibility sufficient that the skirt does not maintain a shape thereof when unsupported. The base is configured to secure the sheath to the penis.

In an embodiment, a fluid collection system is disclosed. The fluid collection system includes a fluid collection assembly. The fluid collection assembly includes a sheath. The sheath includes a proximal end defining an opening configured to receive at least a urethral opening of a penis. The sheath also includes a distal end opposite the first end defining an aperture. Additionally, the sheath includes a fluid impermeable barrier extending from the proximal end to the distal end. The fluid impermeable barrier at least partially defines a chamber extending between the opening that is configured to receive at least the urethral opening of the penis. The sheath further includes at least one porous material disposed in the chamber. The fluid collection assembly also includes a base including a skirt configured to secure the base to the individual. The skirt exhibits a flexibility sufficient that the skirt does not maintain a shape thereof when unsupported. The base is configured to secure the sheath to the penis. The fluid collection system also includes a fluid storage container in fluid communication with the aperture of the sheath, the fluid storage container positioned downstream from the fluid collection assembly. Further, the fluid collection system includes a vacuum source configured to apply a suction force to the chamber. The vacuum source is in fluid communication with the fluid storage container.

In an embodiment, a method of using a fluid collection assembly is disclosed. The method includes positioning at least the urethral opening of the penis through the opening and into the chamber of a fluid collection assembly. The fluid collection assembly includes a sheath. The sheath includes a proximal end defining an opening configured to receive at least a urethral opening of a penis. The sheath also includes a distal end opposite the first end defining an aperture. Additionally, the sheath includes a fluid impermeable barrier extending from the proximal end to the distal end. The fluid impermeable barrier at least partially defines a chamber extending between the opening that is configured to receive at least the urethral opening of the penis. The sheath further includes at least one porous material disposed in the chamber. The fluid collection assembly also includes a base including a skirt configured to secure the base to the individual. The skirt exhibits a flexibility sufficient that the skirt does not maintain a shape thereof when unsupported. The base is configured to secure the sheath to the penis. The method also includes positioning at least the urethral opening of the penis of the individual through the hole of the skirt and securing the skirt to a skin about the penis of the individual.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

US 12,629,276 B2

3

Figure 6:
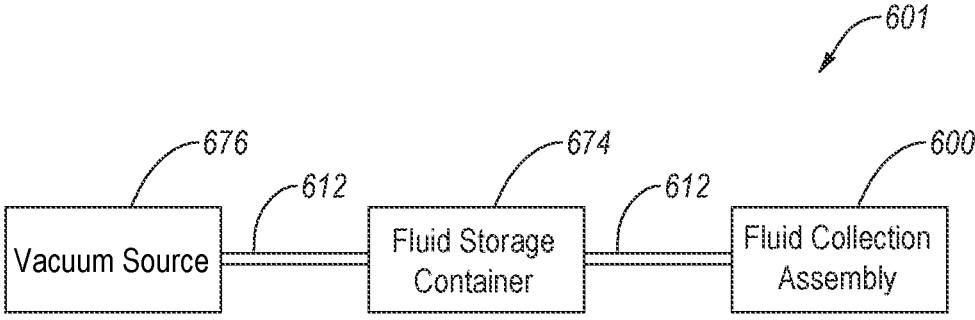

FIG. 6 is a block diagram of a fluid collection system, according to an embodiment.

DETAILED DESCRIPTION

Fluid collection assemblies including a skirt, fluid collection systems including the same, and methods of using the same are disclosed herein. An example fluid collection assembly (e.g., a condom-style male catheter) includes a sheath defining an opening. The sheath includes a fluid impermeable barrier at least partially defining at least a portion of a chamber and at least one porous material disposed in the chamber. The opening and the chamber of the fluid collection assembly are configured to receive at least a portion of a penis (e.g., at least the urethral opening of the penis). The fluid collection assembly also includes a skirt. The skirt is configured to attach the fluid collection assembly to an individual. To facilitate attachment to the individual, the skirt may exhibit a high flexibility, such as a flexibility that is sufficient that the skirt does not maintain a shape thereof when unsupported (e.g., unsupported by the base, a detachable support layer, the skin about the penis, or other structure). The high flexibility allows the skirt to be comfortably attached to the skin about the penis even when the size and/or topography of the skin about the penis varies or changes due to movement of the individual.

Some fluid collection assemblies may be configured to be attached to individuals using a relatively rigid base. The relatively rigid base exhibits sufficient rigidity to maintain the shape thereof when unsupported. It is noted that the relatively rigid base may exhibit a flexibility that allows it to be bent, flexed, or otherwise deformed. The relatively rigid base of the conventional fluid collection assemblies may be attached to skin of an individual about the penis using an adhesive or by resting the relatively rigid base on the skin about the penis. However, the skin of the individual about the penis may exhibit a size and/or topography that varies from one individual to the next. In an example, attaching the relatively rigid base to the skin about the penis with an adhesive may be uncomfortable because the relatively rigid base is likely pull or press on the skin about the penis since the skin about each penis will inherently exhibit different sizes and/or topographies than the relatively rigid base. In an example, merely positioning the relatively rigid base on the skin about the penis (e.g., not attaching the relatively rigid base to the skin about the penis with an adhesive) is likely to create gaps between the relatively rigid base and the skin about the penis through which bodily fluids (e.g., urine) may flow. The gaps may be caused by wrinkles or variations in the size and/or topography of the skin about the penis. Further, the individual is likely to move and the movement of the individual will change the size and/or topography of the skin about the penis thereby causing the relatively rigid base to pull on the skin about the penis or create gaps between the relatively rigid base and the skin about the penis.

The high flexibility of the skirt disclosed herein may remedy at least some of the problems discussed above with regards to the relatively rigid base. For example, the high flexibility of the skirt allows the skirt to conform to the size and topography of the skin about the penis. For instance, the skirt to be attached to the skin about the penis with an adhesive and the skirt may pull or press on the skin about the penis significantly less than the relatively rigid base due to the high flexibility of the skirt. Further, the skirt may continue to conform to the size and/or topography of the skin about the penis when the individual moves due the high flexibility of the skirt which makes the skirt more comfortable to use than the relatively rigid base. Further, the high flexibility of the skirt allows the skirt to conform to the topography of the skin about the penis thereby inhibiting the formation of gaps between the skirt and the skin about the penis through which bodily fluids may flow, even when the individual moves.

Figure 1A:
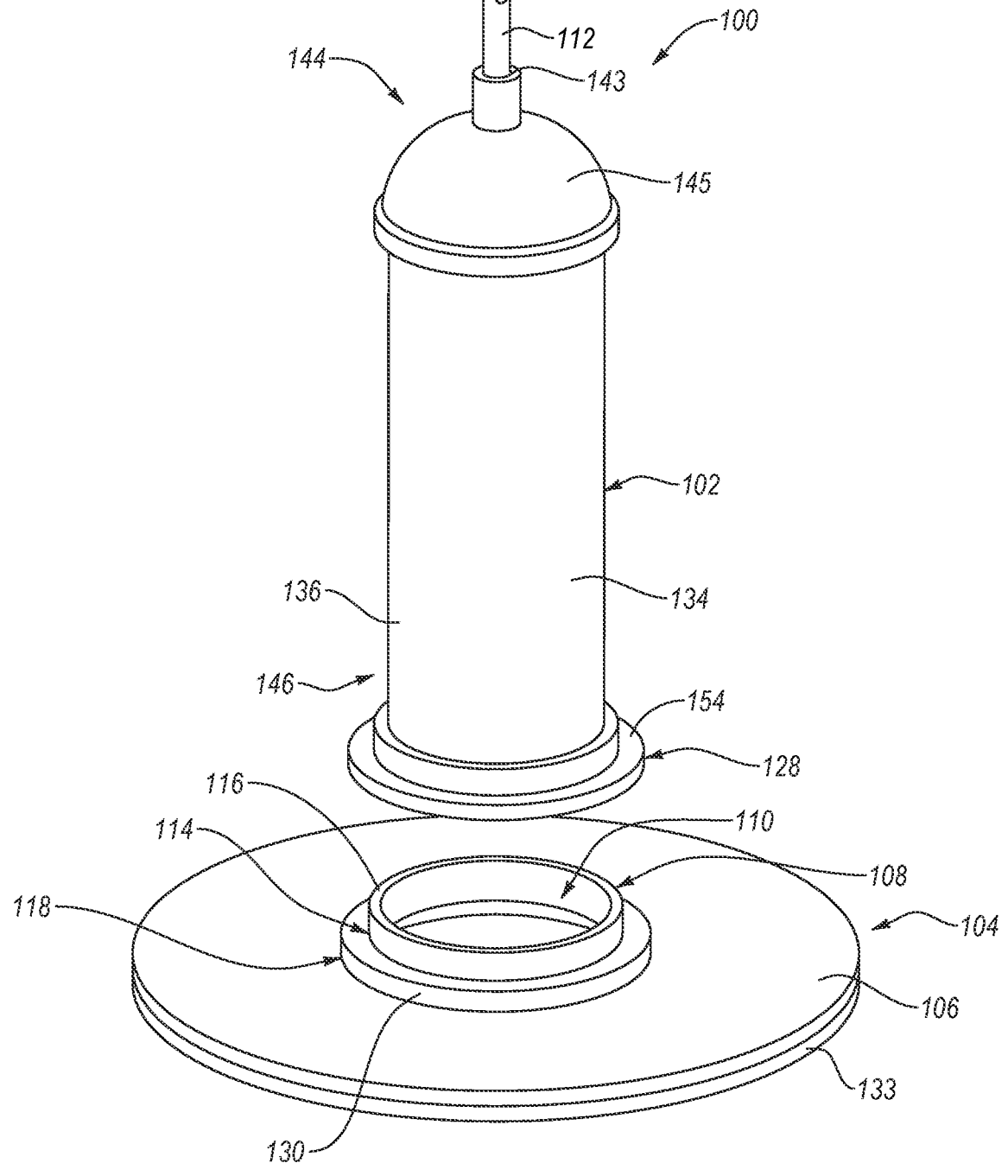
FIGS. 1A and 1B are isometric and cross-sectional views, respectively, of a fluid collection assembly, according to an embodiment.
Figure 1B:
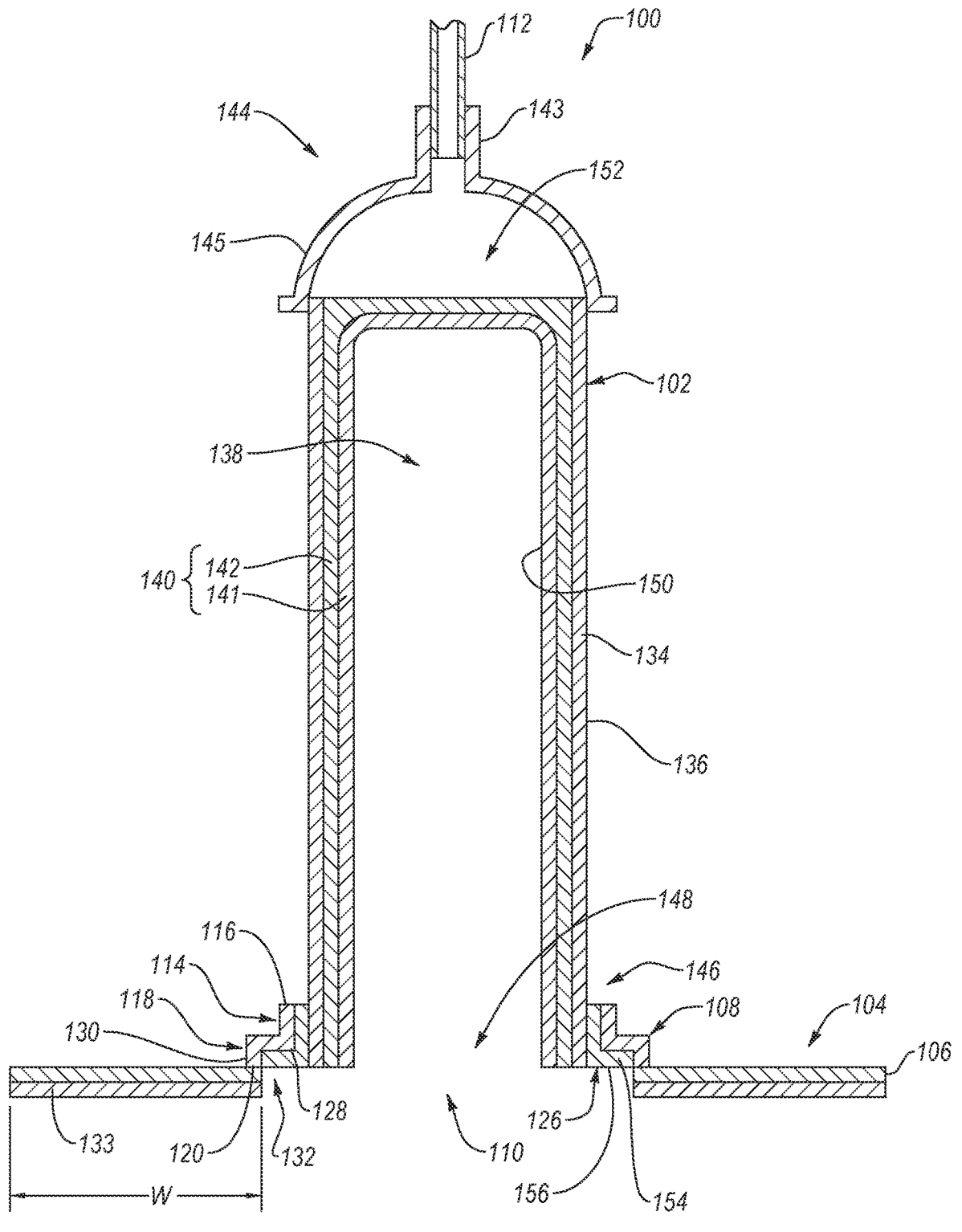

FIGS. 1A and 1B are isometric and cross-sectional views, respectively, of a fluid collection assembly 100, according to an embodiment. The fluid collection assembly 100 includes a sheath 102 and a base 104. The sheath 102 may be configured to receive at least the urethral opening of a penis when the penis is not buried. The base 104 is sized, shaped, and made of a material to be coupled to skin that surrounds the penis and have at least the urethral opening of the penis positioned therethrough when the penis is not buried. For example, the base 104 includes a skirt 106 that is configured to be coupled to the skin that surrounds the penis. The base 104 also defines aperture 110 that is configured to receive (e.g., seal against) the sheath 102 thereby securing the sheath 102 to the penis. For example, the skirt 106 is configured to attach the base 104 to the skin about the penis which, in turn, allows the base 104 to maintain the sheath 102 about the penis. In an embodiment, as shown in FIG. 1A, the sheath 102 and the base 104 are spaced from each other, such as before or after the fluid collection assembly 100 is used. In an embodiment, as shown in FIG. 1B, the sheath 102 is partially disposed in the base 104, such as during operation of the fluid collection assembly 100.

The base 104 is releasably coupleable to sheath 102. For example, the base 104 may include a rigid structure 108. The rigid structure 108 is a portion of the base 104 that is more rigid than the skirt 106 which allows the rigid structure 108 to maintain a shape thereof and facilitates attaching the sheath 102 to the base 104. The relatively small size of the rigid structure 108 relative to the skirt 106 minimizes the ability of the rigid structure 108 to pull on the skin about the penis or form gaps through which the bodily fluids may leak. The rigid structure 108 defines aperture 110 that is configured to receive the sheath 102. For example, the aperture 110 also exhibits a size that is sufficient to have a portion of the sheath 102 disposed therein. The rigid structure 108 can also be configured to maintain the sheath 102 in a particular position and/or at a particular angle relative to the individual's body (e.g., the skin about the penis) via, for example, releasable frictional engagement between the sheath 102 and the rigid structure 108. For instance, the rigid structure 108 can be configured to maintain the sheath 102 at an angle that is greater than 90° (e.g., about 120°), less than 90° (e.g., about 60°), or 90° relative to an axis running along the length of a user lying supine. The different angles that the rigid structure 108 maintains the sheath 102 may be selected to prevent kinking of the tube 112 and/or may be selected based on the angle that the individual's penis extents when erect which may make wearing the fluid collection assembly 100 more comfortable.

In an embodiment, the aperture 110 of the rigid structure 108 allows the sheath 102 to rotate within the rigid structure 108 as the individual using the fluid collection assembly 100 moves (e.g., rotates from side to side). In such an embodiment, the shape of the sheath 102 and the aperture 110 of the rigid structure 108 exhibit a circular cross-section (e.g., a generally cylindrical or conical shape) since other cross-sectional shapes, such as oblong shapes, can inhibit rotation of the sheath 102 in the aperture 110. Rotating the sheath 102 within the aperture 110 of the rigid structure 108 can enable the sheath 102 to be oriented in the direction of the tube 112, thereby preventing kinks in the tube 112, prevent leaks forming between the individual and the sheath 102, etc., as the individual moves.

The rigid structure 108 and/or the sheath 102 can be configured to enable the sheath 102 to rotate in the aperture 110 of the rigid structure 108 using any suitable method. In an embodiment, the aperture 110 of the rigid structure 108 can exhibit a size and shape that corresponds to, but is slightly larger than the sheath 102 which can enable the sheath 102 to rotate in the aperture 110 of the rigid structure 108. It is noted that any gap formed between the rigid structure 108 and the sheath 102 is sufficiently small to substantially inhibit fluid flow therethrough. However, any gap between the rigid structure 108 and the sheath 102 may be configured allow air to flow therein. In an embodiment, the rigid structure 108 and/or the sheath 102 are configured to minimize friction therebetween which can facilitate rotation of the sheath 102 in the aperture 110 of the stabilization accessory. For example, the rigid structure 108 and/or the sheath 102 can at least one of be polished, include a low friction material, or include a lubricant that at least partially coats a surface thereof.

The rigid structure 108 may include a generally vertical flange 114 (e.g., annular flange) defining a top surface 116 of the rigid structure 108. In an embodiment, the rigid structure 108 may also include a generally horizontal flange 118 (e.g., annular flange) defining a bottom surface 120 of the rigid structure 108. The generally vertical flange 114 may extend upwardly from the generally horizontal flange 118 and the generally horizontal flange 118 may extend radially outwardly from the generally vertical flange 114.

The generally vertical flange 114 and the generally horizontal flange 118 of the rigid structure 108 define at least a portion of the aperture 110 of the base 104. The size and shape of the portion of the aperture 110 that is defined by the generally vertical flange 114 and the generally horizontal flange 118 may substantially corresponds to the size and shape of a portion of the sheath 102 (e.g., ring 128) to prevent bodily fluids from flowing through a gap between the rigid structure 108 and the sheath 102. It is noted that the size and shape of the portion of the aperture 110 that is defined by the generally vertical flange 114 and the generally horizontal flange 118 may be slightly greater than the size and shape of a portion of the sheath 102 to allow air to flow therebetween.

Referring to FIG. 1B, the portions of the generally vertical flange 114 and the generally horizontal flange 118 that define the aperture 110 may also be configured to secure the sheath 102 thereto. In an example, the aperture 110 may exhibit a first diameter at or near the bottom surface 120 and a second diameter at or near the top surface 116 that is less than the first diameter. The variation in the diameter of the aperture 110 may secure the sheath 102 to the rigid structure 108 when the sheath 102 includes a similar variation in the diameters thereof. For instance, the aperture 110 may include a first portion extending from the bottom surface 120 that exhibits the first diameter, a second portion extending from the top surface 116 that exhibits the second diameter that is smaller than the first diameter, and a step 126 at the intersection between the first and second portions caused by the difference in the first and second diameters. As will be discussed in more detail below, the first portion, the second portion, and the step 126 may secure the sheath 102 to the rigid structure 108 when the sheath 102 includes a ring 128.

In an embodiment, as illustrated, at least a portion of the bottom surface 120 of the rigid structure 108 is configured to be attached to the skirt 106. The bottom surface 120 may be attached to the skirt 106 using any suitable method. For example, the bottom surface 120 may be attached to the skirt 106 via heat staking, ultrasonic welding, an adhesive, or any other suitable method. The skirt 106 may be more strongly attached to the bottom surface 120 than the skin about the penis such that the skirt 106 is preferentially detached from the skin about the penis when an individual detaches the base 104 from the skin about the penis by pulling on the rigid structure 108.

The bottom surface 120 may exhibit a surface area that is sufficient to allow the bottom surface 120 to be securely attached to the skirt 106. For example, the bottom surface 120 may exhibit a surface area that is great than about 0.25 cm$^2$, greater than about 1 cm$^2$, greater than about 2 cm$^2$, greater than about 3 cm$^2$, greater than about 5 cm$^2$, greater than about 7.5 cm$^2$, greater than about 10 cm$^2$, greater than about 15 cm$^2$, greater than about 20 cm$^2$, greater than about 25 cm$^2$, greater than about 30 cm$^2$, greater than about 40 cm$^2$, greater than 50 cm$^2$, less than about 75 cm$^2$, less than about 50 cm$^2$, less than about 40 cm$^2$, less than about 30 cm$^2$, less than about 20 cm$^2$, less than 15 cm$^2$, less than about 10 cm$^2$, less than about 7.5 cm$^2$, less than about 5 cm$^2$, less than about 3 cm$^2$, less than about 2 cm$^2$, or in in ranges of about 0.25 cm$^2$ to about 1 cm$^2$, about 0.5 cm$^2$ to about 1.5 cm$^2$, about 1 cm$^2$ to about 2 cm$^2$, about 1.5 cm$^2$ to about 3 cm$^2$, about 2 cm$^2$ to about 4 cm$^2$, about 3 cm$^2$ to about 5 cm$^2$, about 4 cm$^2$ to about 7 cm$^2$, about 5 cm$^2$ to about 10 cm$^2$, about 7.5 cm$^2$ to about 15 cm$^2$, about 10 cm$^2$ to about 20 cm$^2$, about 15 cm$^2$ to about 25 cm$^2$, about 20 cm$^2$ to about 30 cm$^2$, about 25 cm$^2$ to about 35 cm$^2$, about 30 cm$^2$ to about 40 cm$^2$, about 35 cm$^2$ to about 45 cm$^2$, about 40 cm$^2$ to about 50 cm$^2$, about 45 cm$^2$ to about 60 cm$^2$, or about 50 cm$^2$ to about 75 cm$^2$. The surface area of the bottom surface 120 may be selected based on a number of factors. In an example, the surface area of the bottom surface 120 may be selected based on the type of attachment between the bottom surface 120 and the skirt 106. For instance, the bottom surface 120 may exhibit a smaller surface area when the bottom surface 120 is attached to the skirt 106 via ultrasonic welding than when the bottom surface 120 is attached to the skirt 106 using an adhesive. Meanwhile, the bottom surface 120 may merely exhibit the surface area needed to heat stake the skirt 106 thereto. In an example, the surface area of the bottom surface 120 may be selected based on the size of the skirt 106 and/or the strength of the adhesive used to secure the skirt 106 to the skin. For instance, increasing the size of the skirt 106 and/or the strength of the adhesive may require an increase in the size of the bottom surface 120 to maintain the attachment between the bottom surface 120 and the skirt 106 when the skirt 106 is detached from the skin. In an example, the surface area of the bottom surface 120 may be selected to be as small as possible since the high rigidity of the bottom surface 120 (relative to the skirt 106) may cause the bottom surface 120 to pull on the region about the individual's penis. Maintaining the surface area of the bottom surface 120 as small as possible may minimize the pulling on the skin about the penis caused by the high rigidity of the bottom surface 120.

In an embodiment, the skirt 106 may be attached to a lateral surface 130 of the rigid structure 108 via heat staking, ultrasonic welding, an adhesive, or any other suitable method. In such an embodiment, at least a portion of the bottom surface 120 may directly contact the individual.

The skirt 106 defines an opening 132. The opening 132 exhibits a dimension (e.g., diameter) that is sufficient to have at least a portion of the penis (e.g., at least the urethral opening of the penis) inserted therethrough when the penis is not buried. Also, the opening 132 may exhibit a dimension that is sufficient to allow the sheath 102 to be positioned therethrough. In the illustrated embodiment, the opening 132 of the skirt 106 exhibits a dimension that is substantially the same as a corresponding dimension of a portion of the aperture 110 of the rigid structure 108 defined by the bottom surface 120 of the rigid structure 108 (e.g., the first diameter of the aperture 110). However, it is noted that the dimension of the opening 132 may be greater than the corresponding dimension of the aperture 110 of the rigid structure 108 defined by the bottom surface 120 or, due to the high flexibility of the skirt 106, the dimension of the opening 132 may be less than the corresponding dimension of the aperture 110 of the rigid structure 108 defined by the bottom surface 120. The opening 132 may exhibit a dimension that is about 1.5 cm to about 5 cm.

The skirt 106 may exhibit a maximum width W measured from the opening 132 to an outer portion of the skirt 106 that is radially spaced from the opening 132. The maximum width W may be greater than about 0.5 cm, greater than about 1 cm, greater than about 1.5 cm, greater than about 2 cm, greater than about 2.5 cm, greater than about 3 cm, greater than about 3.5 cm, greater than about 4 cm, greater than about 4.5 cm, greater than about 5 cm, greater than about 6 cm, greater than about 7 cm, greater than about 8 cm, greater than about 9 cm, greater than about 10 cm, greater than about 15 cm, greater than about 20 cm, less than about 25 cm, less than about 20 cm, less than about 15 cm, less than about 10 cm, less than about 7.5 cm, less than about 5 cm, or in ranges of about 0.5 cm to about 1.5 cm, about 1 cm to about 2 cm, about 2.5 cm to about 3.5 cm, about 3 cm to about 4 cm, about 3.5 cm to about 4.5 cm, about 4 cm to about 5 cm, about 4.5 cm to about 6 cm, about 5 cm to about 7 cm, about 6 cm to about 8 cm, about 7 cm to about 9 cm, about 8 cm to about 10 cm, about 9 cm to about 15 cm, about 10 cm to about 20 cm, or about 15 cm to about 25 cm. The maximum width W of the skirt 106 may depend on the strength of the adhesive that is used to attach the skirt 106 to the skin about the penis, whether the skin about the penis is hairy or shaved, and the overall size of the skin about the penis. In some embodiments, the maximum width W of the skirt 106 may be the radius or diameter of the skirt 106.

The skirt 106 may exhibit an intended topography. The intended topography of the skirt 106 may be substantially planar, exhibit a partial spherical shape, exhibit a topography that corresponds to a typical topography of the skin about a penis, or any other suitable topography. The skirt 106 exhibits the intended topography thereof when the tensile and compressive forces applied to the skirt 106 are at a minimum (e.g., the tensile and compressive forces are zero). The skirt 106 may only exhibit the intended topography thereof when the skirt 106 is supported due to the high flexibility of the skirt 106. The skirt 106 also exhibits a relaxed topography. The relaxed topography of the skirt 106 is the topography that the skirt 106 exhibits when the skirt 106 is unsupported. The relaxed topography of the skirt 106 may vary. The skirt 106 exhibits high flexibility when the intended topography of the skirt 106 is significantly different than the relaxed topography of the skirt 106. The intended topography of the skirt 106 is significantly different than the relaxed topography of the skirt 106 when at least a portion of the skirt 106 is displaced by at least about 1 cm (e.g., at least about 2 cm, at least about 3 cm, at least about 4 cm, at least about 5 cm, at least about 7 cm, at least about 10 cm, at least about 15 cm, at least about 20 cm, or in ranges of about 1 cm to about 3 cm, about 2 cm to about 4 cm, about 3 cm to about 5 cm, about 4 cm to about 7 cm, about 5 cm to about 10 cm, about 7.5 cm to about 15 cm, or about 10 cm to about 20 cm) when the skirt 106 switches between the intended topography and the relaxed topography. The amount that the portion of the skirt 106 is displaced may depend on the maximum width W of the skirt 106. For example, the intended topography of the skirt 106 is significantly different than the relaxed topography of the skirt 106 when the displacement between the two topographies is at least 25% of the maximum width W, at least 50% of the maximum width W, at least 75% of the maximum width W, or at least 100% the maximum width. In an embodiment, the intended topography of the skirt 106 is significantly different than the relaxed topography of the skirt 106 when the intended topography does not include one or more wrinkles (i.e., easily visible ridges) while the relaxed topography does include one or more wrinkles. In an embodiment, the intended topography of the skirt 106 is significantly different than the relaxed topography of the skirt 106 when at least a portion of the skirt 106 is closer to being parallel to the direction of gravity than being parallel to the intended topography.

The high flexibility of the skirt 106 may depend on a number of factors, such as at least one of the thickness of the skirt 106 or the Young's modulus of the material that forms the skirt. In an embodiment, the skirt 106 may exhibit a thickness that is less than about 2 mm, less than about 1 mm, less than about 750 μm, less than about 500 μm, less than about 300 μm, less than about 200 μm, less than about 100 μm, less than about 50 μm, less than about 25 μm, less than about 10 μm, less than about 5 μm, less than about 1 μm, or in ranges of about 1 μm to about 10 μm, about 5 μm to about 25 μm, about 10 μm to about 50 μm, about 25 μm to about 100 μm, about 50 μm to about 200 μm, about 100 μm to about 300 μm, about 200 μm to about 500 μm about 300 μm to about 750 μm, about 500 μm to about 1 mm, or about 750 μm to about 2 mm. In an embodiment, the skirt 106 may include a material exhibiting a Young's modulus that is less than about 3 GPa, such as less than about 2.5 GPa, less than about 2 GPa, less than about 1.5 GPa, less than about 1 GPa, less than about 0.5 GPa, less than about 0.1 GPa, less than about 0.05 GPa, or in ranges of about 0.01 GPa to about 0.1 GPa, about 0.05 GPa to about 0.5 GPa, about 0.1 GPa to about 1 GPa, about 0.5 GPa to about 1.5 GPa, about 1 GPa to about 2 GPa, about 1.5 GPa to about 2.5 GPa, or about 2 GPa to about 3 GPa, since such materials may exhibit a high flexibility when also exhibiting any of the thicknesses disclosed above. It is noted that, in some embodiments, the Young's modulus of the material of the skirt 106 may be greater than 3 GPa, especially at some of the thicknesses discussed above. In an embodiment, the skirt 106 may include a material exhibit a percent elongation that is greater than about 50%, greater than about 75%, greater than about 100%, greater than about 150%, greater than about 200%, greater than about 300%, greater than about 500% or in ranges of about 50% to about 100%, about 75% to about 150%, about 100% to about 200%, about 150% to about 300%, or about 200% to about 500% which will allow the skirt 106 to exhibit larger deformations (e.g., caused by movement of the individual) without failing. In an embodiment, the skirt 106 is formed from a thermoplastic (e.g., PVC, PTFE, polypropylene, nylon, polyethylene) since thermoplastics may be softer and more flexible than other materials. In an embodiment, the skirt 106 may be formed from a biocompatible material and/or a hypoallergenic material since the skirt 106 is configured to come in contact with the skin of the individual. In an embodiment, the skirt 106 is formed from tegaderm.

In an embodiment, the skirt 106 is formed from a breathable material. The breathable material of the skirt 106 may allow air and/or moisture to flow through the skirt 106 thereby allowing the portions of the skin of the individual that contact the skirt 106 to remain drier than if the skirt 106 was not formed of a breathable material. In an example, the breathable material that forms at least a portion of the skirt 106 defines a plurality of pores, such as a fabric or nonwoven material. In an example, the breathable material that forms at least portion of the skirt 106 includes tegaderm.

The base 204 includes a backing 133 attached to the skirt 106. The backing 133 is configured to be detached from the skirt 106 substantially without damaging the skirt 106.

The sheath 102 includes (e.g., may be formed from) a fluid impermeable barrier 134 that is sized and shaped to fit into the aperture 110 of the rigid structure 108. For example, the sheath 102 may be generally tubular or cup-shaped. The generally tubular or cup-shaped fluid impermeable barrier 134 may at least partially define the outer surface 136 of the sheath 102. The fluid impermeable barrier 134 may define an opening 148 extending through the fluid impermeable barrier 134 that is configured to have at least a portion of a penis positioned therethrough.

The fluid impermeable barrier 134 at least partially defines a chamber 138 (e.g., interior region). For example, the interior surface(s) 150 of the fluid impermeable barrier 134 at least partially defines the chamber 138 within the fluid collection assembly 100. The fluid impermeable barrier 134 temporarily stores the fluid(s) in the chamber 138. The fluid impermeable barrier 134 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 134 substantially prevents the fluid(s) from passing through the fluid impermeable barrier 134. In an example, the fluid impermeable barrier 134 may be air permeable and fluid impermeable. In such an example, the fluid impermeable barrier 134 may be formed of a hydrophobic material that defines a plurality of pores. At least one or more portions of at least an outer surface 136 of the fluid impermeable barrier 134 may be formed from a soft and/or smooth material, thereby reducing chaffing.

The fluid impermeable barrier 134 at least partially defines the chamber 138. For example, the inner surface 150 of the fluid impermeable barrier 134 at least partially defines the perimeter of the chamber 138. The chamber 138 may at least temporarily retain fluids therein.

As shown, the fluid collection assembly 100 may include at least one porous material 140 therein. The porous material 140 may be configured to wick any fluid away from the opening 148, thereby preventing the fluid from escaping the chamber 138. The permeable properties referred to herein may be wicking, capillary action, diffusion, or other similar properties or processes, and are referred to herein as "permeable" and/or "wicking." Such "wicking" may not include absorption of fluid into the porous material 140. Put another way, substantially no absorption of fluid into the material may take place after the material is exposed to the fluid and removed from the fluid for a time. While no absorption is desired, the term "substantially no absorption" may allow for nominal amounts of absorption of fluid into the porous material 140 (e.g., absorbency), such as less than about 10 wt % of the dry weight of the porous material 140, less than about 7 wt %, less than about 5 wt %, less than about 3 wt %, less than about 2 wt %, less than about 1 wt %, or less than about 0.5 wt % of the dry weight of the porous material 140. The porous material 140 may also wick the fluid generally towards an interior of the chamber 138, as discussed in more detail below. In an embodiment, the porous material 140 may include at least one absorbent and/or at least one adsorbent material.

The porous material 140 may include one or more of a fluid permeable membrane 141 or a fluid permeable support 142. The fluid permeable membrane 141 is disposed in the chamber 138. The fluid permeable membrane 141 may be configured to contact the penis when at least a portion of the penis is disposed in the chamber 138. The fluid permeable membrane 141 may be composed to wick fluid dispensed into the chamber 138 away from the opening 148 (e.g., towards at least one of the fluid impermeable barrier 134 or an inlet of the tube 112) thereby preventing the fluid from escaping the chamber 138.

The fluid permeable membrane 141 may include any material that may wick the fluid. For example, the fluid permeable membrane 141 may include fabric, such as a gauze (e.g., a silk, linen, or cotton gauze), another soft fabric, or another smooth fabric. Forming the fluid permeable membrane 141 from gauze, soft fabric, and/or smooth fabric may reduce chaffing caused by the fluid collection assembly 100.

The fluid collection assembly 100 may include the fluid permeable support 142 disposed in the chamber 138. The fluid permeable support 142 is configured to support the fluid permeable membrane 141 since the fluid permeable membrane 141 may be formed from a relatively foldable, flimsy, or otherwise easily deformable material. For example, the fluid permeable support 142 may be positioned such that the fluid permeable membrane 141 is disposed between the fluid permeable support 142 and the fluid impermeable barrier 134. As such, the fluid permeable support 142 may support and maintain the position of the fluid permeable membrane 141. The fluid permeable support 142 may include any material that may wick the fluid, such as any of the fluid permeable membrane materials disclosed herein above. For example, the fluid permeable membrane material(s) may be utilized in a more dense or rigid form than in the fluid permeable membrane 141 when used as the fluid permeable support 142. The fluid permeable support 142 may be formed from any fluid permeable material that is less deformable than the fluid permeable membrane 141. For example, the fluid permeable support 142 may include a porous polymer (e.g., nylon, polyester, polyurethane, polyethylene, polypropylene, etc.) structure, woven fibers (e.g., spun nylon fibers, nonwoven fibers, or an open cell foam. In some examples, the fluid permeable support 142 may be formed from a natural material, such as cotton, wool, silk, or combinations thereof. In such examples, the material may have a coating to prevent or limit absorption of fluid into the material, such as a water repellent coating. In some examples, the fluid permeable support 142 may be formed from fabric, felt, gauze, or combinations thereof. In some examples, the fluid permeable membrane 141 may be optional. For example, the porous material 140 may include only the fluid permeable support 142. In some examples, the fluid permeable support 142 may be optionally omitted from the fluid collection assembly 100. For example, the porous material 140 base may only include the fluid permeable membrane 141.

The fluid permeable support 142 may have a greater ability to wick fluids than the fluid permeable membrane 141. In some examples, the wicking ability of the fluid permeable support 142 and the fluid permeable membrane 141 may be substantially the same.

The fluid permeable membrane 141 and the fluid permeable support 142 do not completely fill the chamber 138 since the chamber 138 is configured to have an unoccupied space that receives at least a portion of the penis. In an example, the porous material 140 may leave a substantially unoccupied space at least one of between the porous material 140 and the fluid impermeable barrier 134 or in the sump 145. In such an example, the fluid collection assembly 100 includes the reservoir 152 (FIG. 1B) disposed in the chamber 138 formed from the substantially unoccupied space between the porous material 140 and at least one of the fluid impermeable barrier 134 or in a sump 145 (e.g., a fluid impermeable material that is attached to and is more rigid than the fluid impermeable barrier 134). The fluid impermeable barrier 134 or the sump 145 may define an outlet 143 that is configured to allow the conduit 112 to be in fluid communication with the reservoir 152.

The reservoir 152 is a substantially unoccupied portion of the chamber 138. The fluid(s) that are in the chamber 138 may flow through the fluid permeable membrane 141 and/or fluid permeable support 142 to the reservoir 152. The reservoir 152 may retain of the fluid(s) therein. The fluid(s) that are in the chamber 138 may flow through the fluid permeable membrane 141 and/or fluid permeable support 142 to the reservoir 152. The fluid impermeable barrier 134 may retain the fluid(s) in the reservoir 152. In some examples (not shown), the fluid collection assembly 100 may include multiple reservoirs, such as a first reservoir located between the fluid impermeable barrier 134 and the porous material 140 and a second reservoir located in the sump 145.

The sheath 102 and fluid impermeable barrier 134 may also include at least one vacuum relief hole that allows the chamber 138 to remain substantially at atmospheric pressure. The at least one vacuum relief hole may be located at any point on the sheath 102, such as near or nearer the opening 148. In some examples (not shown), the vacuum relief hole may extend through the sump 145 or be disposed beneath the sump 145. In some examples, the fluid collection assembly 100 may not include the vacuum relief hole, such as when a more complete seal as desired for the chamber 138.

The sheath 102 also includes at least a portion of the tube 112 therein, such as at least partially disposed in the chamber 138. In an example, the tube 112 may extend from the sheath 102 at the distal region 144 to a proximal region 146 at least proximate to the opening 148. The proximal region 146 may be disposed near or on the skin around the penis (e.g., on the penis or pubic area therearound). Accordingly, when a patient lays on their back, fluid (e.g., urine) may aggregate near the opening 148 of the sheath 102 against the skin of the subject. The fluid may be removed from the chamber 138 via the tube 112. In an example, the fluid impermeable barrier 134 may be constructed of a material and/or have a thickness that allows the sheath 102 to collapse when placed under vacuum, such as to remove air around a penis in the fluid collection assembly 100 during use. In such examples, the tube 112 may extend only to or into the distal region 144 in the chamber 138 (e.g., not through to the area adjacent the opening 148). In such examples, urine may be collected and removed from the fluid collection assembly 100 at the end nearest the outlet 143.

The sheath 102 may include a ring 128 at or near the proximal region 146 of the sheath 102 (e.g., at or near the opening 148 of the sheath 102). The ring 128 can be more rigid than the sheath 102. For example, the ring 128 can be formed from a flexible polymer that is at least one of thicker than the entire sheath 102 or a material exhibiting a Young's modulus that is greater than sheath 102. As such, the ring 128 can provide some structure at or near the open proximal region 146 of the sheath 102. The increased rigidity of the ring 128 can cause the opening 148 to remain open thereby facilitating insertion of at least a portion of a penis into the chamber 138.

Further, in an embodiment, the increased rigidity of the ring 128 can enable the ring 128 to secure the sheath 102 in the aperture 110 of the base 104. For example, as illustrated, the ring 128 can include at least one protrusion 154 (e.g., annular protrusion) that extends outwardly from the rest of the ring 128. The protrusion 154 may exhibit a lateral dimension (e.g., diameter) that is sufficiently small that the protrusion 154 may be disposed in the first portion of the aperture 110 exhibiting the first diameter. However, the dimension of the protrusion 154 may be too large to fit into the second portion of the aperture 110 exhibiting the second diameter. In other words, the step 126 may limit the movement of the protrusion 154 in the aperture 110 thereby allowing the sheath 102 to be secured in the aperture 110. In an example, the ring 128 may exhibit a feature instead of or in conjunction with the protrusion 154 that facilitates securement of the sheath 102 in the aperture 110. In such an example, the feature that facilitates securement of the sheath 102 in the aperture 110 may include threads (e.g., the base 104 includes corresponding threads), a recess (e.g., the base 104 includes a corresponding protrusion), or any other suitable feature.

Further examples of features of the fluid collection assembly 100 are disclosed in U.S. patent application Ser. No. 16/433,773 filed on Jun. 6, 2019, the disclosure of which is incorporated herein, in its entirety, by this reference.

Figure 2:
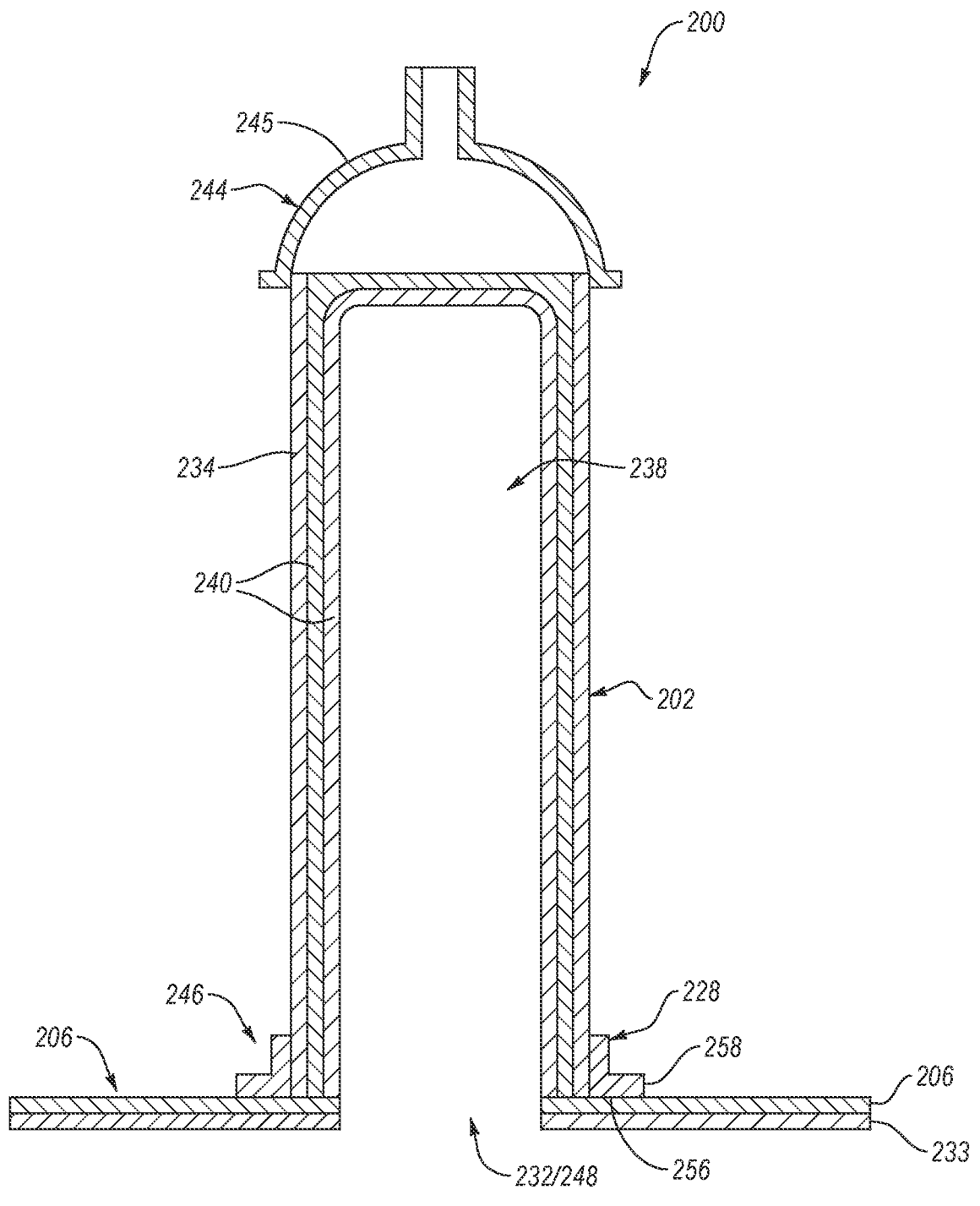
FIG. 2 is a cross-sectional view of a fluid collection assembly that does not include a rigid structure, according to an embodiment.

In some embodiments, the rigid structure may be omitted from the fluid collection assembly. FIG. 2 is a cross-sectional view of a fluid collection assembly 200 that does not include a rigid structure, according to an embodiment. Except as otherwise disclosed herein, the fluid collection assembly 200 is the same or substantially similar to any of the fluid collection assemblies disclosed herein. For example, the fluid collection assembly 200 may include a sheath 202 and a base 204. The sheath 202 may include a fluid impermeable barrier 234 defining a chamber 238, at least one porous material 240 disposed in the chamber 238, a sump 245 at and/or near a distal region 244 of the sheath 202, and a ring 228 at and/or near a proximal region 246 of the sheath 202. The base 204 includes a skirt 206 and backing 233 reversibly attached to the skirt 206. The skirt 206 is directly attached to the sheath 202 at and/or near the proximal region 246 of the sheath 202.

In the illustrated embodiment, the skirt 206 is directly attached to the ring 228. For example, the ring 228 may include a bottom surface 256. The skirt 206 may be directly attached to the bottom surface 256 using any of the same attachment techniques discussed above with regards to attaching the skirt 206 to the rigid structure 108 of FIGS. 1A and 1B. For example, the skirt 206 may be heat staked to the ring 228. The bottom surface 256 may exhibit a surface area that is sufficient to allow the bottom surface 256 to be securely attached to the skirt 206. For example, the bottom surface 256 may exhibit a surface area that is great than about 0.25 cm², greater than about 1 cm², greater than about 2 cm², greater than about 3 cm², greater than about 5 cm², greater than about 7.5 cm², greater than about 10 cm², greater than about 15 cm², greater than about 20 cm², greater than about 25 cm², greater than about 30 cm², greater than about 40 cm², greater than 50 cm², less than about 75 cm², less than about 50 cm², less than about 40 cm², less than about 30 cm², less than about 20 cm², less than 15 cm², less than about 10 cm², less than about 7.5 cm², less than about 5 cm², less than about 3 cm², less than about 2 cm², or in in ranges of about 0.25 cm² to about 1 cm², about 0.5 cm² to about 1.5 cm², about 1 cm² to about 2 cm², about 1.5 cm² to about 3 cm², about 2 cm² to about 4 cm², about 3 cm² to about 5 cm², about 4 cm² to about 7 cm², about 5 cm² to about 10 cm², about 7.5 cm² to about 15 cm², about 10 cm² to about 20 cm², about 15 cm² to about 25 cm², about 20 cm² to about 30 cm², about 25 cm² to about 35 cm², about 30 cm² to about 40 cm², about 35 cm² to about 45 cm², or about 40 cm² to about 50 cm². It is noted that the ring 228 may include a protrusion 254 even though the ring 228 is not attached to a rigid structure since the protrusion 254 increases the surface area of the bottom surface 256 and may facilitate heat staking the skirt 206 to the ring 228. The surface area of the bottom surface 256 may be selected based on a number of factors. In an example, the surface area of the bottom surface 256 may be selected based on the type of attachment between the bottom surface 256 and the skirt 206. For instance, the bottom surface 256 may exhibit a smaller surface area when the bottom surface 256 is attached to the skirt 206 via ultrasonic welding than when the bottom surface 256 is attached to the skirt 206 using an adhesive. Meanwhile, the bottom surface 256 may merely exhibit the surface area needed to heat stake the skirt 206 thereto. In an example, the surface area of the bottom surface 256 may be selected based on the size of the skirt 206 and/or the strength of the adhesive used to secure the skirt 206 to the individual. For instance, increasing the size of the skirt 206 and/or the strength of the adhesive may require an increase in the size of the bottom surface 256 to maintain the attachment between the bottom surface 256 and the skirt 206 when the skirt 206 is detached from the individual. In an example, the surface area of the bottom surface 256 may be selected to be as small as possible since the high rigidity of the bottom surface 256 (relative to the skirt 206) may cause the bottom surface 256 to pull on the skin about the individual's penis. However, maintaining the surface area of the bottom surface 256 as small as possible may minimize the pulling on the skin about the individual's penis caused by the higher rigidity of the bottom surface 256 relative to the skirt 206.

The ring 228 may include at least one lateral surface 258 extending upwardly from the bottom surface 256. In an embodiment, the skirt 206 may be directly attached to the lateral surface 258 instead of or in conjunction with directly attaching the skirt 206 to the bottom surface 256 of the ring 228. In such an embodiment, the skirt 206 may be attached to the lateral surface 258 using any of the attachment techniques disclosed herein.

In an embodiment, the skirt 206 may be directly attached one or more components of the sheath 202 instead of or in conjunction with directly attaching the skirt 206 to the bottom surface 256 and/or lateral surface 258 of the ring 228. For example, the skirt 206 may be directly attached to at least one of the fluid impermeable barrier 234 or the porous material 240.

Figure 3:
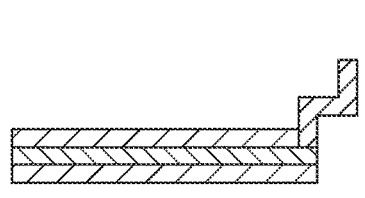
FIG. 3 is a cross-sectional view of a base that includes a support attached to at least a portion of the skirt, according to an embodiment.
Figure 3:
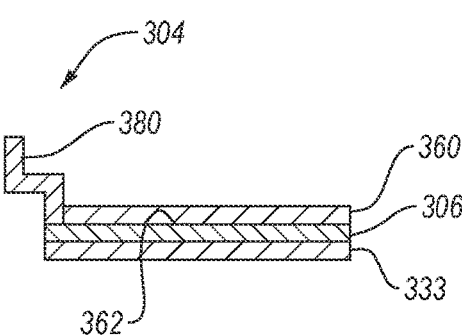

As previously discussed, the skirts disclosed herein exhibit a high flexibility. The high flexibility of the skirts may make attaching the skirts to the skin about the penis difficult. For example, the high flexibility of the skirt may make it difficult to attach the skirt to the skin without forming wrinkles in the skirt at locations where the skirt inadvertently attached to itself. As such, in some embodiments, the base of the fluid collection assemblies disclosed herein may include a support attached to at least a portion of the skirt that provides rigidity to the skirt. FIG. 3 is a cross-sectional view of a base 304 that includes a support 360 attached to at least a portion of the skirt 306, according to an embodiment. Except as otherwise disclosed herein, the base 304 is the same or substantially similar to any of the bases disclosed herein. For example, the base 304 may include the skirt 306 and a backer 333. In the illustrated embodiment, the base 304 includes a rigid structure 308 and the skirt 306 is directly attached to the rigid structure 308. However, it is noted that the rigid structure 308 may be omitted from the base 304 and, instead, the skirt 306 may be directly attached to a sheath (not shown).

The support 360 is attached to at least a portion of the skirt 306, such as attached to at least a portion of at least one upper surface 362 of the skirt 306. The support 360 is more rigid than the skirt 306. As such, the support 360 provides rigidity to the skirt 306 which may make the skirt 306 easier to handle. For example, the skirt 306, when unsupported by the support 360, may be difficult to controllably handle due to the high flexibility thereof. When the backer 333 is removed from the skirt 306, the difficulty in controllably handling the skirt 306 may cause the skirt 306 to inadvertently attach to itself thereby forming wrinkles. Further, the difficulty in controllably handling the skirt 306 may cause the skirt 306 to be inadvertently attached to the wrong location. Detaching the skirt 306 from the wrong location may be painful, damage the skirt 306, and/or may weaken any subsequent attachments between the skirt 306 and skin. However, the support 360 may make the skirt 306 more easy to controllably handling thereby remedying or at least inhibiting these problems.

The support 360 may be formed from any suitable material. In an embodiment, the support 360 is formed from at least one material that exhibits a Young's modulus that is greater than the skirt 306. Examples of such materials may include paper, cardboard, selected polymers, or metal foils. In an embodiment, the support 360 exhibits a thickness that is greater than the skirt 306 which decreases the flexibility of the support 360 relative to the skirt 306.

The increased rigidity of the support 360 may cause the skirt 306 to pull on the region about the penis after the skirt 306 is attached to the skin about the penis. As such, the support 360 is configured to be detached from the skirt 306 substantially without damaging the skirt 306 after the skirt 306 is attached to the skin about the penis. For example, the support 360 may be attached to the skirt 306 using a relatively weak adhesive. The relatively weak adhesive may be selected to be weaker than an attachment between the skirt and the skin about the penis. Thus, pulling on the support 360 may preferentially detach the support 360 from the skirt 306 without detaching the skirt 306 from the skin about the penis. In an embodiment, the support 360 may include one or more regions that are not attached to the skirt 306, such as one or more tabs. The one or more regions may provide a location to grip the support 360 when detaching the support 360 from the skirt 306.

As previously discussed, the high flexibility of the skirts disclosed herein allows the skirt to be more comfortably attached to the skin about an penis regardless of the topography or size of the skin about the penis. However, the size of the skirt may be selected to adequately secure the skirt to the skin about the penis and improve the comfort of using the skirt. For example, the skirt may need to exhibit a size that allows the skirt to be adequately secured to the region about the penis and may make leaks more difficult. Generally, increasing the size of the skirt allows the skirt to be better secured to the skin about the penis. However, increasing the size of the skirt more than necessary may affect the comfort of the skirt. For example, increasing the size of the skirt such that the skirt is attached to the thighs may cause the skirt to pull on thighs when the individual moves. Since the distance from the penis to the thighs vary, it may be beneficial to selected the size of the skirts to, for example, exhibit a large size to better secure the skirt to the skin about the penis and prevent leaks while also exhibiting a small enough size that the skirt does not become attached to the thighs of the individual.

Figure 4A:
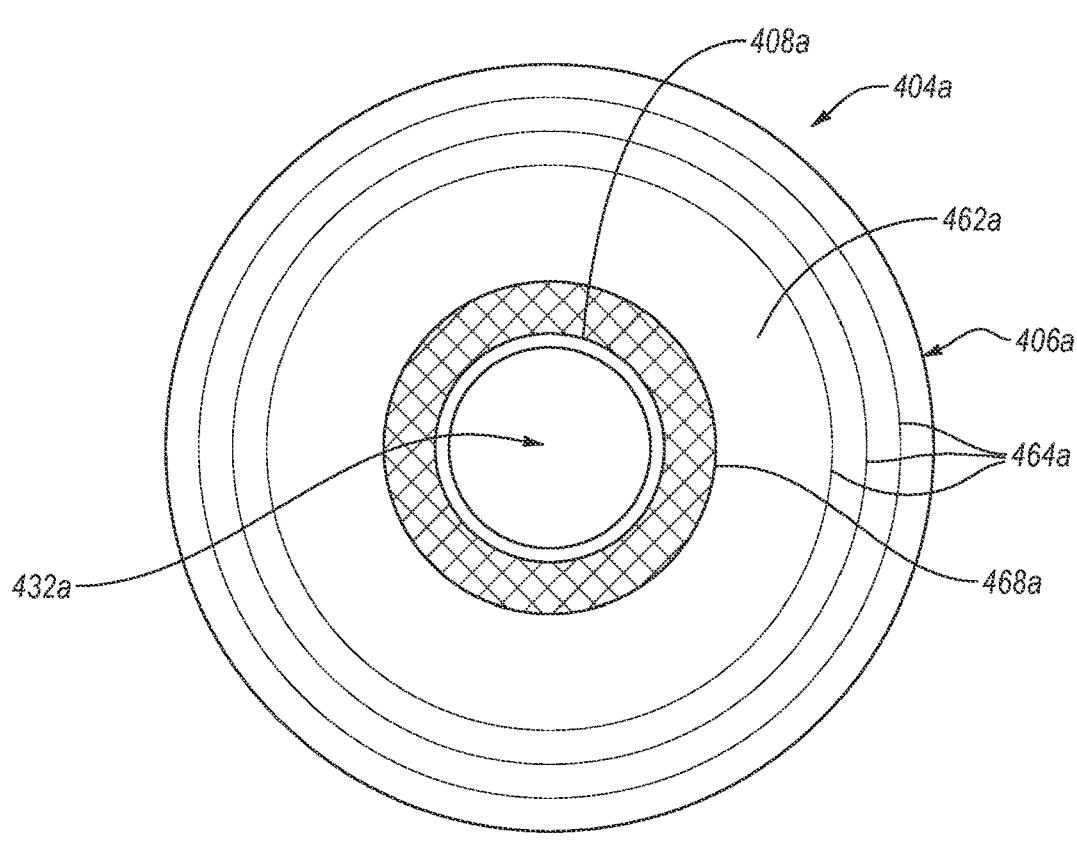
FIG. 4A is a top plan view of a base including a skirt that is configured to fit a plurality of pubic regions exhibiting different sizes, according to an embodiment.

In an embodiment, the fluid collection assemblies disclosed herein may be provided with different sizes of skirts, thereby allowing the skirt to exhibit a size selected for different sized pubic regions (i.e., skin about the penis). For example, the fluid collection assemblies may be provided with a small, medium, or large sizes. However, providing the fluid collection assemblies with different sizes of skirts may require a large inventory of skirts and increases the risk that fluid collection assemblies of a certain size are out of stock. In an embodiment, the fluid collection assemblies disclosed herein may be provided with a skirt having a single size that is configured to fit a plurality of pubic regions exhibiting different sizes. In such an embodiment, the skirt may be configured to be cut. For example, FIG. 4A is an example of a base 404a including a skirt 406a that is configured to fit a plurality of pubic regions exhibiting different sizes, according to an embodiment. Except as otherwise disclosed herein, the base 404a may be the same or substantially similar to any of the bases disclosed herein. For example, the base 404a includes a rigid section 408a and a skirt 406a attached to the rigid section 408a. However, as previously discussed, it is noted that the rigid section 408a may be omitted from the base 404a and the skirt 406a may be directly attached to a sheath (not shown).

The skirt 406a exhibits an initial size. For example, the initial size may be larger than the size of the average pubic region. In the illustrated embodiment, the initial size of the skirt 406a corresponds to an "extra-large" size, though there is no such requirement. The skirt 406a is configured to be cut such that the skirt 406a may exhibit at least one pre-selected size that is different than the initial size. An individual cutting the skirt 406a may have difficultly cutting the skirt 406a from the initial size to the pre-selected size accurately without guidance. For example, the individual cutting the skirt 406a may inadvertently cut the skirt 406a at least one of to the wrong shape (e.g., an oblong shape instead of the illustrated circular shape) which may make placing and securing the skirt 406a to the individual without causing leaks difficult, too small which may require the base 404a to be discarded instead of being use, or too large which may require additional cuts to be made in the skirt 406a. As such, the skirt 406a may include one or more cut lines 464a configured to facilitate cutting of the skirt 406a to a correct pre-selected size. The cut lines 464a may correspond to a single pre-selected size that is different than the initial size or, as illustrated, a plurality of pre-selected sizes that are each from the initial size and each other. In the illustrated embodiment, the skirt 464 includes three cut lines 464a that may correspond to "large," "medium", and "small" sizes, though there is no such requirement.

The cut lines 464a may be formed on the skirt 406a using any suitable technique. In an embodiment, the cut lines 464a may printed on a top surface 462a of the skirt 406a. In an embodiment, when the skirt 406a is transparent, the cut lines 464a may be printed on a bottom surface of the skirt 406a which allows the backer (not shown) to protect the cut lines 464a from being worn or rubbed off. In an embodiment, the cut lines 464a may be formed from recesses formed in the skirt 406a (e.g., thinned regions of the skirt) or ridges extending from the rest of the skirt 406a. The recesses formed in the skirt 406a may be configured to allow the skirt 406a to be torn using hands instead of a cutting instrument (e.g., scissors or knife). In an embodiment, the cut lines 464a are stickers applied to a surface (e.g., top or bottom surface) of the skirt 406a. In an embodiment, the cut lines 464a may be perforations extending partially or completely through the skirt 406a, which may allow the skirt 406a to be torn using hands instead of a cutting instrument. In an embodiment, the cut lines 464a are formed from a combination of the above techniques. For example, the cut lines 464a may be formed from a recess and the recess is at least partially filled with ink printed onto the recess. In such an example, the recess may protect the ink from being worn off while increasing the contrast of the recess.

The cut lines 464a are generally formed on a region of the skirt 406a that is spaced from an opening 432a of the skirt 406a. For example, cutting a region of the skirt 406a that is proximal to the opening 432a of the skirt 406a may inhibit the functionality of the skirt 406a by preventing the skirt 406a from being securely attached to the region about the penis and/or increasing the likelihood that the base 404a leaks. As such, the skirt 406a may include one or more functionality lines 468a that indicate a region of the skirt 406a that should not be cut since cutting into the region may inhibit the functionality of the skirt 406a. Generally, the functionality lines 468a extend outwardly for a distance from the opening 432a of the skirt 406a. The functionality lines 468a may be formed in the skirt 406a using any of the techniques discussed above with regards to the cut lines 464a.

Figure 4B:
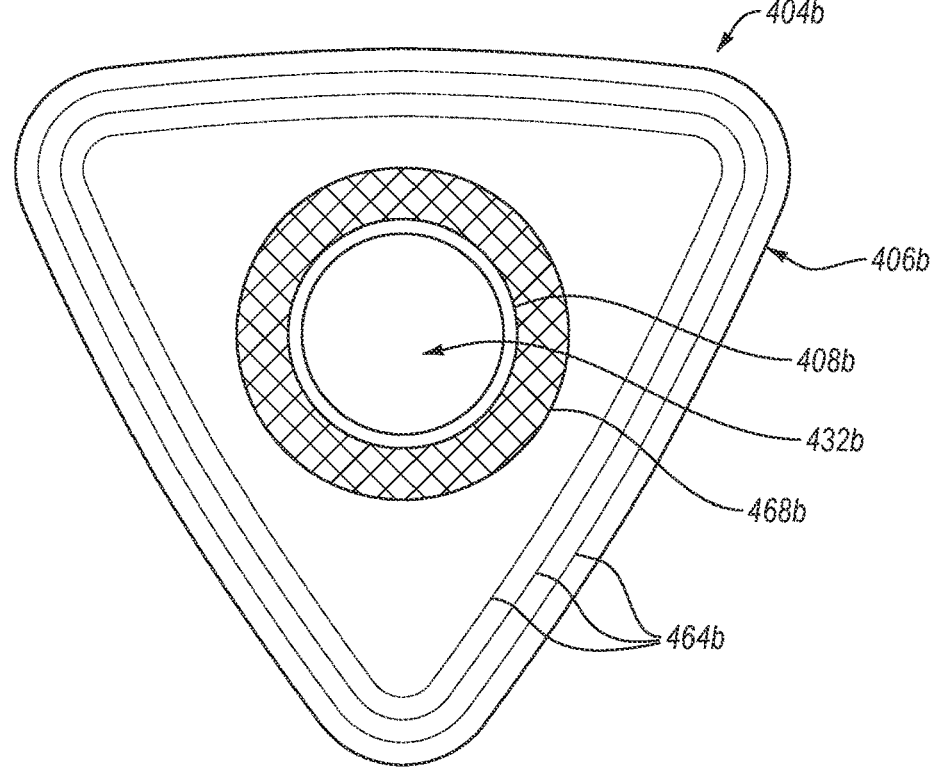
FIG. 4B is a top plan view of a base, according to an embodiment.

The skirt 406a exhibits a generally circular shape and the cut lines 464a also exhibit a generally circular shape. However, at least one of the skirt 406a or at least one of the cut lines 464a may exhibit a non-circular shape. For example, FIG. 4B is a top plan view of a base 404b, according to an embodiment. Except as otherwise disclosed herein, the base 404b may be the same or substantially similar to any of the bases disclosed herein. For example, the base 404b includes a skirt 406b and the skirt 406b may include one or more cut lines 464b or one or more functionality lines 468b lines formed thereon. The base 404b may also include a rigid section 408b though, as previously discussed, the rigid section 408b may be omitted from the base 404b.

The skirt 406b exhibits a generally triangular shape. The generally triangular shape of the skirt 406b may generally correspond to the generally triangular shape of the pubic region. As such, the generally triangular shape of the skirt 406b may allow the skirt 406b to be secured to a larger portion of the pubic region than a generally circular skirt without also being attached to a thigh. The opening 432b of the skirt 406b is illustrated as being centrally located on the skirt 406b. However, it is noted that the opening 432b may be located non-centrally (e.g., closer to one apex of the generally triangular shape than the other two apexes) since the area below the penis (e.g., closer to the anus) may be smaller than an area above the penis (e.g., towards the navel).

As previously discussed, the skirt 406b may include one or more cut lines 464b formed thereon. For example, the skirt 406b may exhibit an initial size. The cut lines 464b may be configured to facilitate reducing the initial size of the skirt 406b to pre-selected sizes. The cut lines 464b exhibit a generally triangular shape that generally corresponds to the generally triangular shape of the initial size of the skirt 406b.

As previously discussed, the skirt 406b may also include one or more functionality lines 468b formed thereon. The functionality lines 468b exhibit a generally circular shape since the skirt 406b generally needs to exhibit a minimum distance from the opening 432b. However, it is noted that the functionality lines 468b may also exhibit a generally triangular shape.

In an embodiment, the skirts disclosed herein may exhibit an initial shape (e.g., a generally circular shape) and the cut lines may exhibit a shape that is different than the initial shape (e.g., a generally triangular shape). In an embodiment, the skirts disclosed herein may exhibit cut lines that exhibit two different shapes, such as at least one cut line exhibiting a generally circular shape and at least one cut line exhibiting a generally triangular shape which allows an individual to select which shape is most beneficial for the particular application. In an embodiment, the skirts and/or cut lines disclosed herein may exhibit a non-circular shape and a non-triangular shape, such as an oblong shape, a generally rectangular shape (e.g., a generally square shape), etc.

Figure 5:
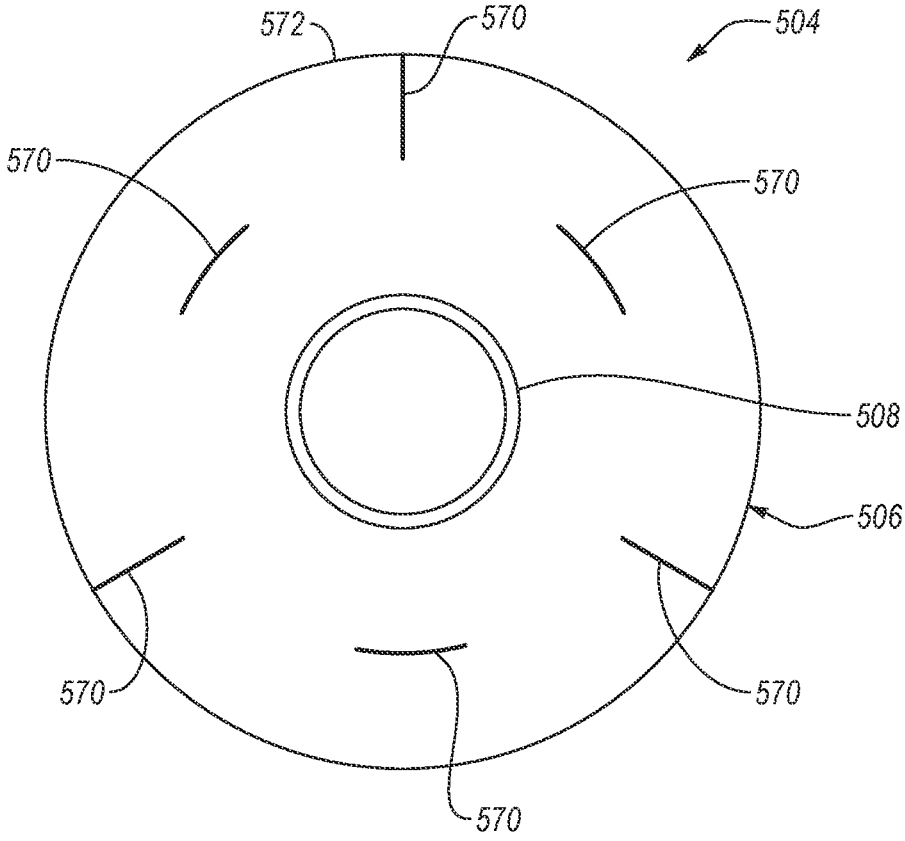
FIG. 5 is a top plan view of a base including a skirt having one or more stress relief features formed therein, according to an embodiment.

The skirts disclosed herein may pull on the individual or may allow leaks even with the high flexibility thereof. For example, certain portions of the skirt may experience significant amounts of stress during use. The stress may be caused by movement of the individual. For instance, the movement of the individual may cause the skirt to pull at areas of significant curvature or at intersections of different body parts (e.g., the intersection between at least two of the pubic region, the thighs, or the iliac region) when the individual moves. The stresses applied to the skirt may cause the skirt to pull on the body, may cause the skirt to warp, or cause the skirt to tear. To minimize the stresses applied to the skirt, the skirt may include one or more stress relief features formed therein. FIG. 5 is a top plan view of a base 504 including a skirt 506 having one or more stress relief features 570 formed therein, according to an embodiment. Except as otherwise disclosed herein, the base 504 is the same or substantially similar to any of the bases disclosed herein. For example, the base 504 may include a rigid section 508 though, as previously discussed the rigid section 508 may be omitted from the base 504 when the skirt 506 is directly attached to a sheath (not shown). Although not shown, the skirt 506 may include one or more cut lines or functionality lines.

As previously discussed, the skirt 506 includes one or more stress relief features 570 formed therein that are configured to reduce stress applied to the skirt 506. In an embodiment, the stress relief features 570 may include cuts (e.g., slits) preformed in the skirt 506. In an embodiment, the stress relief features 570 may include recesses (e.g., regions of the skirt 506 with reduced thickness) or perforations formed in the skirt 506 that are configured to split when a selected stress is applied thereto. In an embodiment, the stress relief features 570 may include lines formed on (e.g., printed on or adhesively applied to) the skirt 506. In such an embodiment, the stress relieve features 570 may indicate regions of the skirt 506 that should be cut to minimize stresses in the skirt 506 which, without the lines, may be difficult or impossible for an individual accurately cut. The lines of the stress relief features 570 may be formed in the skirt 506 using any of the same techniques discussed above with regards to the cut lines. One benefit of forming the stress relief features 570 using lines instead of pre-formed cuts is that a medical practitioner using the skirt 506 has the option of using the stress relief features 570 if the medical practitioner determines that the stress relief features 570 are necessary.

The stress relief features 570 (e.g., the pre-formed cuts, split regions, or cuts made along the lines) allow additional movement in the skirt 506 without additional stresses. The stress relief features 570 may be selected to be at or near locations of the skirt 506 that, without the stress relief features 570, are expected to experience large amounts of stress. In an example, as shown the illustrated embodiment, the stress relief features 570 may include three radially extending stress relief features 570 extending inwardly from a radially outer surface 572 of the skirt 506. The three radially extending stress relief features 570 may be configured to be located at or near the intersection of the thighs with the pubic region and/or the iliac region since these regions may be subjected to significant displacement when an user of the base 504 moves. In an example, as shown in the illustrated embodiment, the stress relief features 570 may include one or more stress relief features 570 that are spaced from the radially outer surface 572 of the skirt 506. In such an example, the three stress relief features 570 may minimize stress caused by the contours of the skin about the penis and the location of these three stress relief features 570 may be selected to be at or near locations where the contours of the skin about the penis are expected to change.

It is noted that the terminal ends of the stress relief features 570, when the terminal ends of the stress relief features 570 end abruptly, may act as stress raisers which may cause tears in the skirt 506 to form at the terminal ends of the stress relief features 570. As such, in some embodiments, the terminal ends of the stress relief features 570 may be rounded (not shown) to prevent the terminal ends of the stress relief features 570 acting as stress raisers. The terminal ends of the stress relief features 570 may be rounded, for example, by pressing a hole into the terminal end of the stress relief features 570.

In an embodiment, the stress relief features 570 may include regions of the skirt 506 exhibiting a higher elasticity that other regions of the skirt 506. Such stress relief features 570 may decrease stress applied to the skirt 506 during movement without cutting the skirt 506 than a substantially similar skirt that does not includes the stress relief features. Examples of stress relief feature 570 that exhibit a higher elasticity that other regions of the skirt 506 includes recesses (e.g., regions of reduced thickness), perforations extending at least partially through the skirt 506, or regions of the skirt 506 formed from material exhibiting a lower Young's modulus that the material(s) forming the rest of the skirt 506.

FIG. 6 is a block diagram of a fluid collection system 601, according to an embodiment. The fluid collection system 601 includes a fluid collection assembly 600 (e.g., any of the fluid collection assemblies disclosed herein), a fluid storage container 674, and a vacuum source 676. The fluid collection assembly 600, the fluid storage container 674, and the vacuum source 676 may be fluidly coupled to each other via one or more conduits 612. For example, fluid collection assembly 600 may be operably coupled to one or more of the fluid storage container 674 or the vacuum source 676 via the conduit 612. Fluid (e.g., urine or other bodily fluids) collected in the fluid collection assembly 600 may be removed from the fluid collection assembly 600 via the conduit 612 which protrudes into the fluid collection assembly 600. For example, an inlet of the conduit 612 may extend into the fluid collection assembly 600, such as to a reservoir therein. The outlet of the conduit 612 may extend into the fluid collection assembly 600 or the vacuum source 676. Suction force may be introduced into the chamber of the fluid collection assembly 600 via the inlet of the conduit 612 responsive to suction (e.g., vacuum) force applied at the outlet of the conduit 612.

The suction force may be applied to the outlet of the conduit 612 by the vacuum source 676 either directly or indirectly. The suction force may be applied indirectly via the fluid storage container 674. For example, the outlet of the conduit 612 may be disposed within the fluid storage container 674 and an additional conduit 612 may extend from the fluid storage container 674 to the vacuum source 676. Accordingly, the vacuum source 676 may apply suction to the fluid collection assembly 600 via the fluid storage container 674. The suction force may be applied directly via the vacuum source 676. For example, the outlet of the conduit 612 may be disposed within the vacuum source 676. An additional conduit 612 may extend from the vacuum source 676 to a point outside of the fluid collection assembly 600, such as to the fluid storage container 674. In such examples, the vacuum source 676 may be disposed between the fluid collection assembly 600 and the fluid storage container 674.

The fluid storage container 674 is sized and shaped to retain a fluid therein. The fluid storage container 674 may include a bag (e.g., drainage bag), a bottle or cup (e.g., collection jar), or any other enclosed container for storing bodily fluid(s) such as urine. In some examples, the conduit 612 may extend from the fluid collection assembly 600 and attach to the fluid storage container 674 at a first point therein. An additional conduit 612 may attach to the fluid storage container 674 at a second point thereon and may extend and attach to the vacuum source 676. Accordingly, a vacuum (e.g., suction) may be drawn through fluid collection assembly 600 via the fluid storage container 674. Fluid, such as urine, may be drained from the fluid collection assembly 600 using the vacuum source 676.

The vacuum source 676 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 676 may provide a vacuum or suction to remove fluid from the fluid collection assembly 600. In some examples, the vacuum source 676 may be powered by one or more of a power cord (e.g., connected to a power socket), one or more batteries, or even manual power (e.g., a hand operated vacuum pump). In some examples, the vacuum source 676 may be sized and shaped to fit outside of, on, or within the fluid collection assembly 600. For example, the vacuum source 676 may include one or more miniaturized pumps or one or more micro pumps. The vacuum sources 676 disclosed herein may include one or more of a switch, a button, a plug, a remote, or any other device suitable to activate the vacuum source 676.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. Structurally or functionally insignificant variations are known to a person having ordinary skill in the art. For example, in some embodiments, a person having ordinary skill in the art would understand that structurally or functional insignificant variations may include varying the quantify modified by the term of degree by ±10%, ±5%, or +2%. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:
a sheath including:
a proximal end defining an opening configured to receive at least a urethral opening of a penis;
a distal end opposite the proximal end defining an aperture;
a fluid impermeable barrier extending from the proximal end to the distal end, the fluid impermeable barrier at least partially defining a chamber extending between the opening that is configured to receive at least the urethral opening of the penis; and
at least one porous material disposed in the chamber; and
a skirt configured to be secured to skin about the penis, the skirt exhibiting a flexibility sufficient that the skirt does not maintain a general shape thereof when unsupported, the skirt configured to secure the sheath to the penis, the skirt including nonwoven fibers.

2. The fluid collection assembly of claim 1, wherein the skirt is directly attached at or near the proximal end of the sheath.

3. The fluid collection assembly of claim 1, further comprising a rigid section directly attached to the skirt, the rigid structure defining an aperture that is configured to receive at least a portion of the sheath.

4. The fluid collection assembly of claim 3, wherein the skirt is at least one of heat staked or ultrasonically welded to the rigid section.

5. The fluid collection assembly of claim 1, wherein the skirt includes an adhesive on a bottom surface thereof.

6. The fluid collection assembly of claim 1, wherein the skirt includes a polyurethan film.

7. The fluid collection assembly of claim 1, wherein the skirt exhibits a generally triangular shape.

8. The fluid collection assembly of claim 1, wherein the skirt includes one or more cut lines formed on the skirt, wherein the one or more cut lines indicate one or more locations of the skirt to be cut.

9. The fluid collection assembly of claim 8, wherein the one or more cut lines corresponding at least one pre-selected size that is different than an initial size of the skirt.

10. The fluid collection assembly of claim 8, wherein the one or more cut lines are spaced from an aperture defined by the skirt, the aperture configured to be aligned with the opening of the fluid impermeable barrier when the skirt is attached to the sheath.

11. The fluid collection assembly of claim 1, wherein the skirt includes one or more functionality lines formed on the skirt, the one or more functionality lines configured to indicate regions of the skirt that should not be cut.

12. The fluid collection assembly of claim 11, wherein the one or more functionality lines surround and abut an aperture defined by the skirt, the aperture configured to be aligned with the opening of the fluid impermeable barrier when the skirt is attached to the sheath.

13. The fluid collection assembly of claim 1, wherein the skirt includes one or more stress relief lines formed on the skirt, the stress relief lines including regions of the skirt exhibiting reduced thickness or perforations formed in the skirt that are configured to split when a selected stress is applied thereto.

14. The fluid collection assembly of claim 1, further comprising a support reversibly attached to at least one upper surface of the skirt, the support configured to maintain a shape of the skirt, wherein the support is only directly attached to the skirt.

15. The fluid collection assembly of claim 14, wherein the support includes at least one of paper or cardboard.

16. The fluid collection assembly of claim 1, wherein the skirt exhibits an intended topography when the skirt is supported and a relaxed topography when the skirt is unsupported, and wherein the skirt exhibits a flexibility sufficient that at least a portion of the skirt exhibits a displacement of at least about 1 cm when the skirt switches from the intended topography and the relaxed topography.

17. The fluid collection assembly of claim 1, wherein the skirt exhibits an intended topography when the skirt is supported, a relaxed topography when the skirt is unsupported, and a maximum width, and wherein the skirt exhibits a flexibility sufficient that at least a portion of the skirt exhibits a displacement of at least about 25% of the maximum width when the skirt switches from the intended topography and the relaxed topography.

18. The fluid collection assembly of claim 1, wherein the skirt is configured to completely surround a penis disposed through the opening.

19. A fluid collection system, comprising:
a fluid collection assembly including;
a sheath including:
a proximal end defining an opening configured to receive at least a urethral opening of a penis;
a distal end opposite the proximal end defining an aperture;
a fluid impermeable barrier extending from the proximal end to the distal end, the fluid impermeable barrier at least partially defining a chamber extending between the opening that is configured to receive at least the urethral opening of the penis; and
at least one porous material disposed in the chamber; and
a skirt configured to be secured to skin about the penis, the skirt including a flexible material, the skirt exhibiting a flexibility sufficient that the skirt does not maintain a general shape thereof when unsupported, the skirt configured to secure the sheath to the penis, the skirt including one or more cut lines formed in the skirt, the one or more cutting lines indicating one or more locations of the skirt to be cut, the one or more cut lines spaced from an aperture defined by the skirt, the aperture configured to be aligned with the opening of the fluid impermeable barrier when the skirt is attached to the sheath;
a fluid storage container in fluid communication with the aperture of the sheath, the fluid storage container positioned downstream from the fluid collection assembly; and
a vacuum source configured to apply a suction force to the chamber, the vacuum source in fluid communication with the fluid storage container.

20. The fluid collection system of claim 19, wherein the skirt includes nonwoven fibers.

21. The fluid collection system of claim 19, further comprising:
at least one first tube extending between the aperture of the fluid collection assembly and the fluid storage container; and
at least one second tube extending between the fluid storage container and the vacuum source.

22. A method of using a fluid collection assembly, the method comprising:
positioning at least a urethral opening of a penis through an opening and into a chamber of the fluid collection assembly, the fluid collection assembly including a sheath, the sheath including a proximal end and a distal end opposite the proximal end, the proximal end defining the opening, the distal end defining an aperture the sheath including a fluid impermeable barrier extending from the proximal end to the distal end, the fluid impermeable barrier at least partially defining the chamber, the sheath further including at least one porous material disposed in the chamber;
positioning at least the urethral opening of the penis of the individual through a hole of a skirt, the skirt including a flexible material, the skirt exhibiting a flexibility sufficient that the skirt does not maintain a general shape thereof when unsupported, the skirt including nonwoven fibers; and
securing the skirt to a skin about the penis of the individual.

23. The method of claim 22, further comprising attaching the fluid collection assembly to the skirt.

* * * * *